United States Patent
Dunn et al.

(10) Patent No.: US 11,657,912 B2
(45) Date of Patent: May 23, 2023

(54) DEVICES, SYSTEMS, AND THEIR METHODS OF USE FOR EVALUATING AND PROCESSING REMUNERATION CLAIMS FROM THIRD-PARTY OBLIGATOR

(71) Applicant: Paradigm Senior Services, Inc., Miami, FL (US)

(72) Inventors: Steven M. Dunn, Bal Harbour, FL (US); Daniel Shapiro, Surfside, FL (US)

(73) Assignee: Paradigm Senior Services, Inc., Miami, FL (US)

( * ) Notice: Subject to any disclaimer, the term of this patent is extended or adjusted under 35 U.S.C. 154(b) by 161 days.

(21) Appl. No.: 16/810,689

(22) Filed: Mar. 5, 2020

(65) Prior Publication Data
US 2020/0286616 A1  Sep. 10, 2020

Related U.S. Application Data

(60) Provisional application No. 62/814,247, filed on Mar. 5, 2019.

(51) Int. Cl.
*G16H 10/60* (2018.01)
*G06N 20/00* (2019.01)
(Continued)

(52) U.S. Cl.
CPC .......... *G16H 40/20* (2018.01); *G06F 16/2365* (2019.01); *G06N 20/00* (2019.01);
(Continued)

(58) Field of Classification Search
CPC ........ G16H 40/20; G16H 10/60; G16H 20/10; G06Q 40/08
See application file for complete search history.

(56) References Cited

U.S. PATENT DOCUMENTS

2010/0063907 A1* 3/2010 Savani ............... G06Q 40/12
705/30
2014/0372141 A1* 12/2014 Renner ............... G06Q 40/08
705/2

FOREIGN PATENT DOCUMENTS

WO  WO-2015042014 A1 *  3/2015  ............. G16H 50/30

OTHER PUBLICATIONS

Miller, Andrew P., et al. "Prior authorization reform for better patient care." (2018): 1937-1939. (Year: 2018).*

* cited by examiner

*Primary Examiner* — Linh Giang Le
*Assistant Examiner* — Constantine Siozopoulos
(74) *Attorney, Agent, or Firm* — James Scott Nolan

(57) ABSTRACT

This document presents devices, systems, and their methods of use for authenticating, evaluating, adjusting, and/or submitting a claim to a third-party obligator. The system may include a client computing device such as a cellular phone, having a downloadable application running thereon. The application running on the client computing device may be configured for generating an interface into which a characterization of treatment to be provided from a healthcare provider to a patient having a third party obligation agreement may be entered, where the obligation agreement includes terms defining coverage for treatments to be provided that will be covered by the agreement. As such, the system may be used to generate a claims submittal packet on behalf of the health care provider for reimbursement from the third party obligator for the treatments provided to the patient by the healthcare provider.

20 Claims, 2 Drawing Sheets

System

(51) Int. Cl.
*G06Q 30/04* (2012.01)
*G06Q 40/08* (2012.01)
*G16H 40/20* (2018.01)
*G06Q 10/10* (2023.01)
*G16H 70/20* (2018.01)
*G16H 50/20* (2018.01)
*G16H 10/20* (2018.01)
*G06Q 50/26* (2012.01)
*G06F 16/23* (2019.01)
*G16H 50/70* (2018.01)

(52) U.S. Cl.
CPC .............. *G06Q 10/10* (2013.01); *G06Q 30/04* (2013.01); *G06Q 40/08* (2013.01); *G06Q 50/26* (2013.01); *G16H 10/20* (2018.01); *G16H 10/60* (2018.01); *G16H 50/20* (2018.01); *G16H 50/70* (2018.01); *G16H 70/20* (2018.01)

System

Process

DEVICES, SYSTEMS, AND THEIR METHODS OF USE FOR EVALUATING AND PROCESSING REMUNERATION CLAIMS FROM THIRD-PARTY OBLIGATOR

CROSS REFERENCE TO RELATED APPLICATIONS

The present application claims priority from U.S. Provisional Patent Application No. 62/814,247, filed Mar. 5, 2019, entitled "DEVICES, SYSTEMS, AND THEIR METHODS OF USE FOR EVALUATING AND PROCESSING REMUNERATION CLAIMS FROM THIRD-PARTY OBLIGATORS", the disclosure of which is incorporated herein by reference in its entirety.

BACKGROUND

This document presents devices, systems, and their methods of use for processing claims, such as claims for remuneration, from a third-party obligator, such as from insurance companies.

Particularly, the generation, submittal, evaluation, and processing of claims for reimbursement forms a large part of the business of health care provision as well as the business of insurance companies. However, there are a wide variety of both health care providers and insurance companies, and there is no systematic manner by which such claims can be submitted. Consequently, such health care providers, along with the insurance companies, require different methods by which claims should be submitted. This results in an increased difficulty and inefficiency for insurance carriers to verify, evaluate, and adjudicate these claims efficiently.

For instance, in various instances, regardless of which methods are used, payment for such claims are often delayed and can be denied for merely technical reasons, due to form rather than substance. Specifically, claims to be submitted must comply with various insurance policy benefits that are associated with the insurance policy of the claimant, and must as well as comply with applicable state and federal government criteria and regulations. If, however, the claim to be submitted, e.g., on behalf of the insured, does not comply in some manner with the government regulations and/or policies. These claims can then be rejected. Moreover, even more of the submitted claims get rejected for the simple reason that they include errors or omit internal insurance provider required information. Such rejections for technical formalities cost time, degrade efficiency, and result in causing trouble, frustration, and harm to the claimant as they are forced to have to wait for authorization and/or re-imbursement for services provided or to be provided. Even when a claim is authorized to be paid upon, there are still a host of reasons by which the full amount of the claim is not reimbursed.

SUMMARY

In one aspect, the present disclosure is directed to devices, systems, and the methods of using the same for evaluating and processing claims on behalf of a patient receiving health treatments from a third-party obligator under an agreement to provide for the proposed treatments. Particularly, in one aspect, provided herein is a system for authenticating, evaluating, adjusting, and/or submitting a claim to a third-party obligator. For example, a system for evaluating and processing claims on behalf of a patient receiving health treatments is provided. The system may include one or more client computing devices, one or more memories forming a structured database, and a server system.

For instance, a first and/or a second client computing device may be provided, such as where the client computing device is configured as, or otherwise coupled with a display. In various instances, the display is configured for displaying a graphical user interface to a first individual using the client computing device. The graphical user interface (GUI) may be configured for generating an interactive dashboard for presentation via the display. Likewise, the interactive dashboard may be configured for performing one or more operations pursuant to the method steps described herein below.

For example, in one embodiment, the GUI may be adapted for presenting an interview to a user, such as a health care provider providing, or a patient seeking, one or more treatment procedures. Particularly, a system server may be provided whereby the server is configured for generating and presenting a healthcare interview to the user so as to determine one or more conditions being experienced by a subject, e.g., patient, and eliciting one or more treatments that could be proposed for the amelioration of the conditions and/or the treatment of the patient. Specifically, the interview may be a claims interview that is generated and provided to the first individual, and in such an instance, the GUI may be configured for receiving responses to the interview from the first individual. In various instances, the claims interview may pertain to a treatment proposed to be administered to the patient in order to treat one or more conditions thereof so as to produce a patient data packet that can be communicated to the system server. Consequently, the client computing device may include a communications module for transmitting the patient data packet via an associated network connection to the server.

Accordingly, the system may include a server that is coupled to the client computing device, via a network interface, which server and/or client computing device may further be coupled, directly or via the network connection, to a database, such as a structured database. The structured database may be adapted so as to form one or more searchable libraries, where each library may include a set of data files pertaining to an obligation agreement between the patient and a third-party obligator. The obligation agreement may include a set of terms that define the coverage for one or more treatments, such as where the structured database is configured for receiving the data packet from the client computing device and/or server.

In various instances, the server system may be configured for generating a project builder, where the project builder may be adapted for providing the graphical user interface to the client computing device, e.g., via the network connection for local display thereby. Particularly, the server system may be configured for performing one or more of the operations described herein. For instance, the server may be configured for generating the claims interview for display at the graphical user interface via the interactive dashboard. As indicated above, the client interview may include one or more interrogatories that are configured for eliciting one or more responses from the first individual so as to produce the patient data packet.

Consequently, the server system may be configured for receiving the patient data packet from the interactive dashboard of the client computing device via the network connection, and once received the sever may be configured for employing the patient data packet in the creation of an individualistic characteristic profile for the patient. The individualistic characteristic profile may include a characterization of one or more conditions of the patient, one or more treatments proposed to be administered to the patient to alleviate the one or more conditions, and one or more terms of the obligation agreement determined to be pertinent to one or more of the conditions of the patient and the one or more treatments proposed to be administered. The one or more proposed treatments include a cost associated with the performance of the treatment.

Once created, the server may then employ the individualistic characteristic profile of the patient to compare the one or more terms of the obligation agreement with the one or more proposed treatments to be administered to the patient, and then determining if there is a conflict between them. Likewise, the server may then determine, based on the results of this comparison, a likelihood that one or more of the proposed treatments to be administered would be covered by the obligation agreement, such as to produce a covered procedure plan. Further, the server may use the covered procedure plan, and the likelihood determination, so as to determine a percentage of the cost that is likely be paid by the third party obligator for each procedure of the proposed treatment so as to generate a total amount to be reimbursed. Additionally, the server may compare the one or more proposed treatments to be administered with the total amount to be reimbursed, and may then authorize one or more of the proposed treatments to be administered based on the likelihood that the one or more proposed treatments will be covered.

In view of the above, in one aspect, provided herein is a system for identifying, authenticating, evaluating, adjusting, and/or submitting a claim to a third-party obligator. For instance, in various embodiments, the system may include one or more, such as a plurality of client computing devices. For instance, in one embodiment, a first client computing device is presented where the client computing device may include an interactive touchscreen display, such as for displaying and/or entering data, such as at a graphical user interface presented at the touch screen display at the first computing device. For instance, the client computing device may be a handheld, mobile computing device, such as a cellular phone, having a downloadable application running thereon. Particularly, the application running on the client computing device may be configured for generating a graphical user interface at the display of the client computing device, into which graphical user interface a characterization of treatment to be provided from a healthcare provider or caretaker to a patient having an obligation agreement with the third party obligator may be entered, such as where the obligation agreement may have one or more terms defining coverage for treatments to be provided that will be covered by the agreement.

In various instances, the system may also include a database, including a memory, such as for storing the obligation agreement along with one or more terms defined by the patient's obligation agreement. Such terms may be converted into one or more rules by which the treatments to be provided can be evaluated against the terms of the obligation agreement. Specifically, the one or more rules may be adapted for determining whether the characterization of the treatment provided corresponds with the one or more terms of the obligation agreement. These rules may be based on one or more of the terms of the obligation agreement, policies of the obligator, county, state, or federal laws, statutes, and/or other regulations. In some instances, the rules may be developed by the system in accordance with how third party obligators actually act, as compared to how they say they are going to act.

Additionally, the system may include a server system having one or more processing engines in communication with the one or more client computing devices and/or the memory. For instance, one of the processing engines may be configured to receive, e.g., from a client computing device, the characterization of treatment provided by a health care professional. Likewise, a processing engine may be configured to retrieve from the memory, the one more rules, such as the one or more rules being identified as being applicable to the patient's obligation agreement and the treatment provided to the patient by the healthcare professional.

The system may also be configured for determining, e.g., by an evaluation engine of the server system, if one or more characteristics of the treatment provided or to be provided to the patient are covered by the one or more terms of the obligation agreement. Additionally the system may be configured for generating, by a claims generating engine of the server system, a claims packet including one or more claims for submittal to the third-party obligator, such as when it is determined that the treatment provided is covered by the one or more terms of the obligation agreement. Once generated, the claims packet may then be submitted to the third-party obligator, by the system server.

Accordingly, provided herein is a system for evaluating and processing claims on behalf of a patient receiving healthcare treatments. As indicated above, the system may include one or more client computing devices, a structured database, and a claims evaluation system server. Particularly, a client computing device may be provided whereby each client computing device includes a display coupled therewith and having a communications module for generating, receiving, and/or transmitting patient data packets via an associated network connection. More particularly, the client computing device may be configured for receiving data pertaining to a treatment proposed by a healthcare provider to be administered to a patient in order to treat one or more conditions thereof so as to produce the patient data packet.

The client computing device may be coupled to the database via a network connection, whereby the computing device may be configured to transmit and the database is configured for receiving, parsing, and/or storing the patient data packet and their contents. In various embodiments, the database may be configured as a structured database, where the structured database may be formed so as to include one or more searchable libraries, such as where each library includes a plurality of data files, such as data files pertaining to an obligation agreement between the patient and a third-party obligator. The data packet may include a variety of data pertaining to the patient, their history, the electronic medical or health records, data pertaining to their family of origins, their environment, and the like. Likewise, the obligation agreement may include a set of terms defining a coverage for one or more treatments. All of this data may be parsed based on its contents, classified, and tagged in accordance with one or more categories so as to generate a variety of data points, whereby each data point may be stored within the database in a structured format, such as within a library pertaining to one or more classifications of the parsed data points.

A server system may also be provided, such as where the serve system may include one or more servers, such as a rack of servers. In various embodiments, a server of the system may be configured for receiving the patient data packet, performing the aforementioned parsing and/or classifying of the identified data points, e.g., for each of the characteristic profile of the individual to be treated, the proposed treatment to be administered, and the terms of the obligation agreement, and for evaluating the various different data points, including comparing the proposed treatment against the obligation agreement so as to determine the likelihood that the proposed treatment will be covered.

As indicated above, in various embodiments, the server system may include one or more, e.g., a plurality of processing engines. For instance, the server system may include a first processing engine, such as for receiving the data packet containing the data pertaining to the proposed treatment, and for identifying one or more procedures to be taken for the purpose of implementing the treatment as well as identifying and/or determining cost associated with each proposed treatment. This data may be received, parsed, one or more data points defined, and may then be transmitted to the structured database for storage. Accordingly, a second processing engine may be provided for retrieving various of the data from the structured database.

For instance, the obligation agreement may be parsed, classified, categorized, and may then be stored in the database, and later can be retrieved as necessary, by searching one or more libraries based on one or more pertinent datafiles. As discussed, the obligation agreement may have one or more terms of coverage that define what is to be covered for that patient, which terms can be used as one or more data points by which the terms of the obligation agreement can be classified, stored, and retrieved. The processing engine, therefore, may be configured for identifying one or more terms in the obligation agreement that may be pertinent to the one or more procedures to be taken. A third processing engine may also be provided for comparing one or more terms, e.g., data points, of the obligation agreement with the one or more procedures to be taken, and determining if there is a conflict between them.

Likewise, a fourth processing engine may further be configured for determining the likelihood that one or more of the procedures proposed to be taken would be covered by the obligation agreement, the result being a determination of coverage, such as containing one or more procedures that are likely to be covered, or an indication that coverage of any of the procedures is unlikely. Hence, form this analysis, a covered procedure plan may be determined, which can then be used to determine the percentage of the cost that is likely be paid on for each procedure so as to generate a total amount to be reimbursed, if the one or more procedures of the covered procedure plan are provided. Consequently, a fifth processing engine may be provided such as for comparing the one or more procedures proposed to be taken with the total amount to be reimbursed, and for determining whether an authorization should be made so as to authorize one or more of the procedures to be taken, such as where the authorization is based on the likelihood that each proposed procedure will be covered.

Once one or more of the procedures have been authorized, and the patient treated in accordance with the authorized procedure plan, a fifth processing engine may be engaged, such as for generating an invoice for the services rendered, which invoice can then be formatted in accordance with one or more rules required by the third party obligator. Likewise, once an invoice has been generated and formatted, the processing engine may then submit the invoice to the third-party obligator, such as where the invoice includes one or more claims for reimbursement, e.g., where each claim includes an amount to be reimbursed. Thus, a processing engine for determining the total amount to be reimbursed may also be included. Additionally, a sixth processing engine may also be provided, such as for determining an immediate amount to be paid to the health care provider on the one or more claims, such as based on the invoice generated and the likelihood of being paid on the invoiced items, and hence, the immediate amount to be paid may be less than the total amount to be reimbursed.

In a further embodiment, the system for authenticating, evaluating, adjusting, and/or submitting claims to the third-party obligator may include both a first and second client computing device, such as where each device includes a downloadable application that runs on the device. As indicated above, the application is configured for generating a graphical user interface that is configured for one or more of entering, retrieving, evaluating, and manipulating data. Accordingly, in various embodiments, the first and second client computing devices may be configured for receiving patient identification information including one or more of an identity of the patient, and a nature of the patient's health issues, as well as the patient's third-party obligation agreement setting out one or more terms of treatment coverage.

In such an instance, the first client computing device may be configured so as to be accessible to a healthcare provider and/or a patient thereof, and may be configured for conducting an electronic, interactive interview of the patient and/or healthcare provider, such as where the answers to the interactive interview process may be used to generate a claim submittal packet, for instance, where the claims packet includes a detailed listing of the patient's condition, a detailed listing of the applicable terms to be applied to the conditions, a preliminary mapping of the terms to the conditions to be applied, and a preliminary determination of one or more claims for reimbursement. Additionally, the second client computing device may be accessible to the third party obligator and may be configured for evaluating the claims packet and one or more claims for submittal, such as in determining if one or more of the claims may be reimbursed. In such an instance, the second computing device may be coupled to the first computing device, such as via a network connection, and can thus, generate and transmits one or more recommendations as to how to improve the claims submittal packet so as to be more acceptable to the third party obligator, such as by highlighting inconsistencies between the patent's conditions and the proposed treatments thereof and/or inconsistencies between one or more claims being proposed to be made and the one or more rules governing the authorization and/or obligations to cover the procedures.

As indicated, such a system may include one or more database, such as where the database is configured for storing the patient identification information, the patient third-party obligation agreement, setting forth one or more terms of the patient's healthcare claim coverage, and one or more rules, such as rules for determining whether the characterization of the treatment provided corresponds with the one or more terms of the obligation agreement. As described in detail herein, all of the entered, or otherwise received, data may be parsed, individually identified, and thus, can be classified and stored within the structured library in accordance with one or more categories thereof. In particular instances, these individually identified data points may be employed by the system so as to generate a knowledge graph data structure whereby various relationships between data points may be defined and weighted. These relationships and the weighting thereof may then be employed by the system so as to generate one or more inferences there from, and using these inferences, one or more initial predictions may be made. These predictions can then be tested so as to derive a predictive model that can then be used to train, such as by employing a machine learning module, the inference module of the system, which once trained can be used for better weighting the various relationships of the knowledge graph, better scoring individual factors thereof, and subsequently producing more accurate likelihood determinations, as discussed herein.

As indicated, the system may include a server system where a server thereof is in communication with one or more of the first and second client computing devices and the database, such as over a network connection. And in particular embodiments, the server system may have one or more processing engines, such as a machine learning and/or inference engine, which may be configured for receiving, from the first and/or second client computing devices, the claim submittal packet and third party obligation agreement and its terms, as well as the data pertaining thereto, and once received the processing engines may further be configured for building and/or otherwise accessing the structured database, so as to generate a score for one or more claims of the claim submittal packet so as to produce one or more scored claims, which can sent back to the first computing device and/or may be used to generate an invoice that can be transmitted to the second client computing device for evaluation thereby.

In another aspect, therefore, provided herein is a non-transitory computer readable medium for storing instructions that, when executed by one or more processors of a computing device of the system, e.g., a client computing device and/or a server, such as a processing engine of a server of the system, so as to cause the one or more processors to perform one or more methods disclosed herein, such as for identifying, authenticating, evaluating, adjusting, and/or submitting claims to the third-party obligator. For instance, the method may include one or more identifying and/or determining steps, which steps may be implemented by one or more processing engines of the server and/or a client computing device. Particularly, the method may include identifying, such as by a processor of a client computing device and/or server, a patient in need of treatment, such as a patient having an agreement with a third-party obligator, e.g., an agreement obligating the third-party obligator to pay for one or more treatments. Additionally the method may include identifying one or more treatments provided or to be provided to the patient, such as by a health care provider, and/or may include identifying one or more provisions in the agreement characterizing the treatments covered by the agreement. Furthermore, in various embodiments, the method may include determining, such as by a processor of a client computing device and/or server, whether the treatment provided is covered by the provisions of the agreement.

Likewise, the non-transitory computer readable medium may include instructions that when executed by one or more processing engines of a server or a client computing device of the system, so as to cause the one or more processors to generate a claim for submittal to the third-party obligator, such as when it is determined that the treatment is covered by one or more terms of the agreement. For these purposes, the generating of a claim may include identifying one or more rules applicable to one or more of the treatment and the provisions of the agreement, and applying the identified rules to the treatment so as to determine whether the treatment provided is covered by the provisions of the agreement. In certain instances, the one or more rules may include a requirement that should be met for receiving payment on the claim. Further, a claim packet including one or more claims for submittal to the third-party obligator may also be generated and submitted.

In various embodiments, the methods to be executed may further include retrieving, e.g., using the one or more computing devices, accurate information, when it is determined that the information in the claim packet is deficient because of it being either missing or inaccurate. In such an instance, the methods may include performing a search of one or more structured libraries of the system, such as based on one or more tagged or other categorical identifiers, so as to identify potential solutions to the observed inconsistencies. And in certain instances, the methods may include a search of the rules database and/or search for current practices being presently engaged in so as to determine if the inconsistency is due to a misapplication of the rules, or to see if a rule change has been initiated, either formally or informally by practice. If no formal rule change has been implemented, and an inconsistency between a rule and a practice is determined, than a flag may be generated to highlight the inconsistency, and/or a recommendation for correcting the inconsistency may be made.

Accordingly, in view of the proceeding, in one aspect, provided herein is a computer implemented method for evaluating and processing claims, e.g., on behalf of a patient receiving, or a healthcare professional providing, healthcare treatments. The method may include one or more of the following steps. For instance, the method may include generating, at a client computer device, a project builder for providing a first graphical user interface to the first client computing device via a network connection for display thereby. The graphical user interface may be configured for generating an interactive dashboard for presentation via the display. The interactive dashboard may be configured for presenting an interview, e.g., a claims interview, to a first individual, e.g., a patient and/or healthcare provider, and for receiving responses thereto from the first individual.

In various embodiments, the claims interview may be an interactive interview whereby answers to previously presented questions may be used by the system to determine subsequent questions to be presented to the first individual. For example, the system may be configured for analyzing patient, condition, and treatment data, as well as obligation terms and rules data so as to generate a graph or a map thereof so as to intuitively build one or more claims, such as to generate a claims packet. Likewise, the system may be configured for reviewing and/or evaluating a generated claim and/or claims packet, and/or for determining inconsistencies there between.

Particularly, the system may include a database of questions that have been known to provide pertinent information for the determination of claims and/or for the resolution of one or more conflicts and/or inconsistencies between a condition of a patient and a proposed treatment, and/or a conflict between a condition or a proposed treatment and one or more terms of the obligation agreement and/or rules associated therewith. Hence, when an inconsistency arises, the computer implemented method may include identifying patient conditions, proposed treatments, proposed term coverage, and applicable rules, and determine the manner of the inconsistency and/or conflict. Then one or more libraries of the structured database may be searched so as to identify and retrieve information that will resolve the conflict, and if the conflict cannot be resolved, a search of the questions library may be performed so as to generate one or more questions that can then be presented to a system user so as to resolve the conflict.

Specifically, the claims interview may be automatically and/or autonomously generated by the system, or by a system user, in a manner so as to include questions pertaining to determining and/or evaluating and/or resolving a conflict related to one or more of a treatment proposed by a healthcare provider to be administered to a patient in order to treat one or more conditions thereof so as to produce a patient data packet and/or to resolve one or more inconsistencies within a previously generated data packet. Where an inconsistency results, but the information necessary to resolve the conflict is determined by the system or a user thereof, then the system may autonomously substitute the correct information into a data packet so as to thereby resolve any issues. In various instances, before such a correction is made, the system may present the proposed correction to a user of the system such as for approval thereby prior to making the correction. Once generated and/or reviewed and/or corrected and approved, the claims data packet can then be transmitted, e.g., via an associated network connection, to one or more other computing devices of the system.

The method, therefore, may include receiving, e.g., at a remote server system coupled to the client computing device via the network connection, the patient data packet from the interactive dashboard. Once received the patient data packet may be employed in the creation of an individualistic characteristic profile for the first individual. The individualistic characteristic profile may include a characterization of one or more conditions of the patient, one or more treatments proposed to be administered to the patient to alleviate the one or more conditions. Likewise, the patient individualistic characteristic profile may further include one or more terms of the obligation agreement that have been determined, e.g., by the system or a user thereof, to be pertinent to one or more of the conditions of the patient and the one or more conditions of the patient. In addition, the method may include a determination of a cost associated with one or more proposed treatments.

Additionally, the method may include employing, by one or more processing engines of the remote server, or other system computing device, the individualistic characteristic profile for the first individual so as to compare one or more terms of the obligation agreement with the one or more of the proposed treatments to be administered to the patient. Such a comparison may be performed, as indicated above, so as to determine if there is a conflict between any of the pertinent data necessary to assure a claim made upon the third party obligator on behalf of the patient and/or healthcare provider is accepted and paid on. Likewise the comparison may be performed so as to assess a likelihood that the one or more proposed treatments will be covered by the obligation agreement, and further determining a percentage of the cost that is likely be paid for each procedure of the proposed treatment so as to generate a total amount expected to be reimbursed. Further still, the method may include generating, based on the assessed likelihood that one or more of the procedures of the proposed treatment will be covered, and further based on what the percentage of the cost will be paid, one or more claims to be included in an invoice, which invoice, and the claims pertaining thereto, may be submitted to the third-party obligator, such as where each of the invoice includes one or more claims for reimbursement, each claim having an amount to be reimbursed.

In view of the preceding, in another aspect, provided herein is a method, such as a computer implemented method, for evaluating a claim for re-imbursement, e.g., to be submitted to a third-party obligator. The method may include one or more of the following steps. For instance, a first step may include, receiving, such as at a system server, a claim for reimbursement from a claimant, which claimant may be a patient, a healthcare provider, or a healthcare providing facility that has been assigned the rights of the patient. The claim may include information characterizing one or more services having been provided to the patient. Additionally, the method may include retrieving, such as by the system server, client computer, or the like, one or more rules from a rules database associated with the system server, e.g., the rules database storing a plurality or rules setting forth a set of requirements for receiving payment of the claim.

Once the one or more rules to be applied by the system has been identified and retrieved, the retrieved rules may be compared to the characterizations of the conditions of the patient, so as to determine if the information of the claim in that regard is accurate or includes a deficiency. The system may then compare the retrieved rules to the characterizations of the one or more services being, or having been, provided so as to determine if the information of the claim in that regard includes a deficiency. If a deficiency is determined, it may then be flagged and/or corrected. Further, once corrected, if needed, then the method may include engaging a score generator of the system so as generate a score representing a likelihood that the claim will be paid upon by the third-party obligator. Particularly, a score generator of the system server, may generate a score for one or more of the claims, such a score representing a likelihood that the one or more claims will be paid upon by the third-party obligator. This data may then be used by the system to authorize a payment to the patient or healthcare provider thereof so as to reimburse them for the services provided, such as prior to receiving reimbursement from the third party obligator.

The details of one or more embodiments are set forth in the accompanying figures and the description below. Other features and advantages will be apparent from the description and drawings, and from the claims.

DETAILED DESCRIPTION

Figure 1:
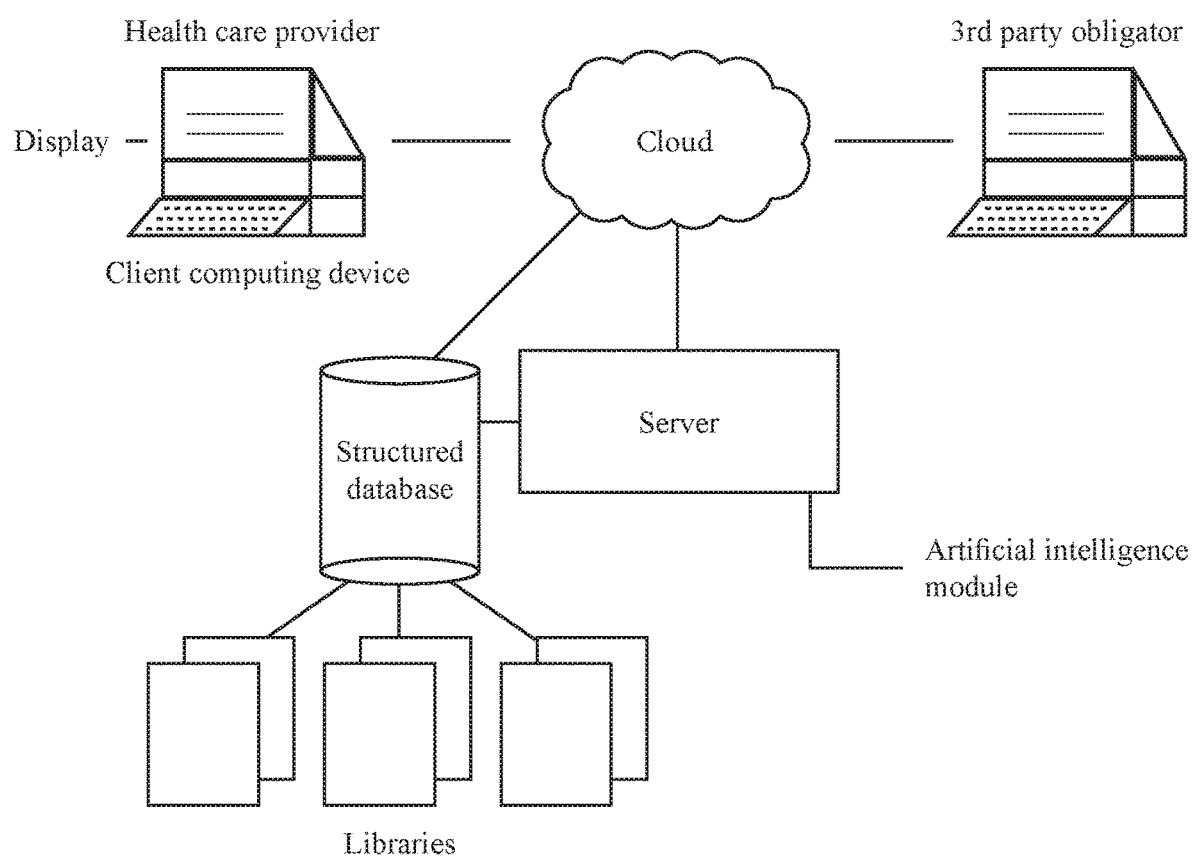
FIG. 1 presents a diagram of an exemplary system of the disclosure.
Figure 2:
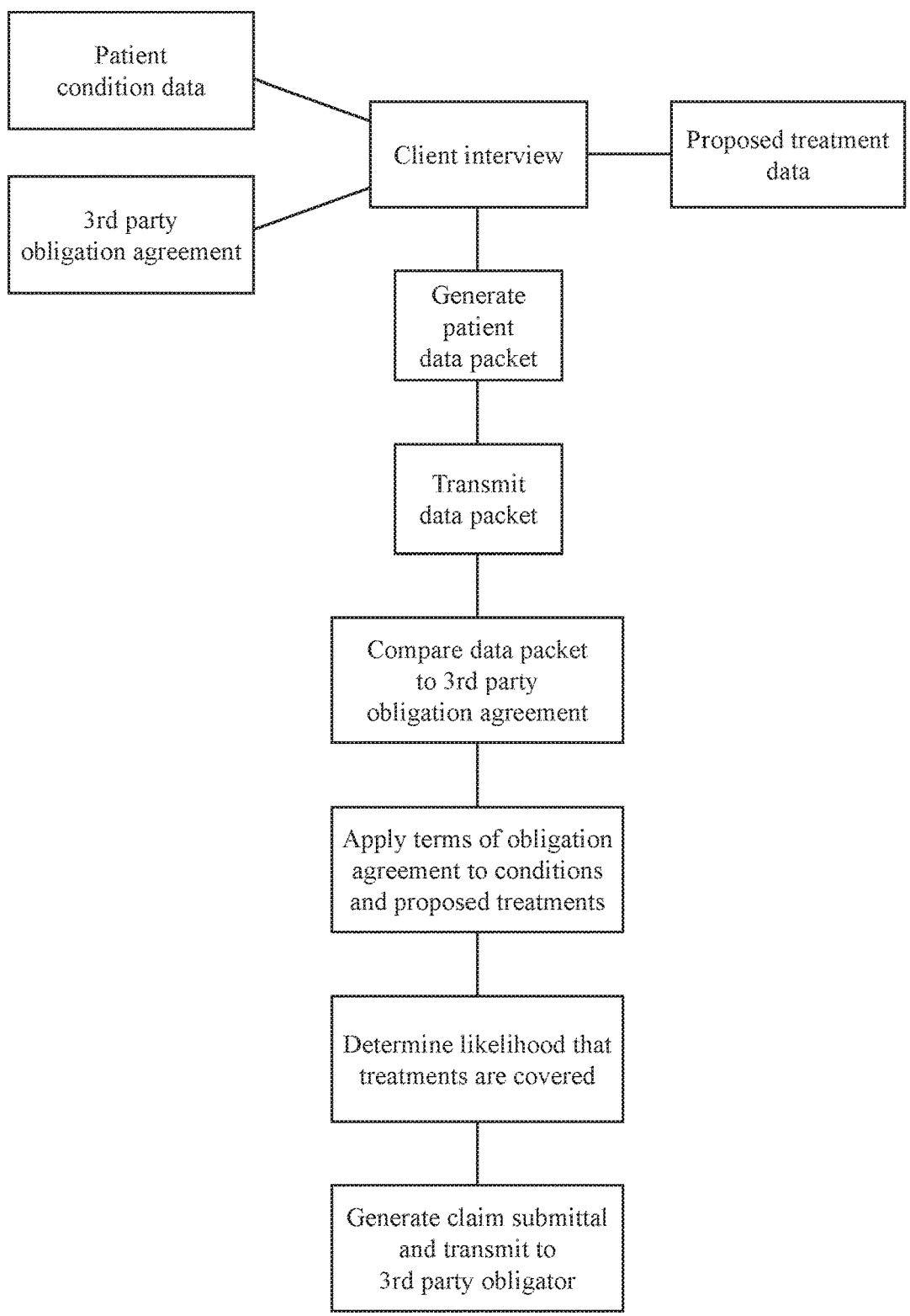
FIG. 2 presents a diagram of an exemplary process of the disclosure.

In one aspect, presented herein are both software and hardware products that are configured for the expeditious generating, tracking, and evaluating of insurance claims by one or more of a health-care agency, a third party obligator, such as an insurance agency, a health care provider, and/or a client, e.g., a patient, of the same be used by the care provider. For instance, there are a variety of different types of health care providing agencies, such as distributed care providers, as well as short, medium, or long term care and/or monitoring services. Distributed care providers operate facilities that allow the ailing to come in and receive care and guidance, when they are not feeling well or need assistance. These providers manage and/or run offices and other facilities for providing urgent and mid-term care to the ailing. Home care agencies and providers serve those requiring medium and long term care.

Often times, the home care provider agency employs and sends home care providers and caregivers into people's homes, so as to provide personal home care to their ailing clients. These home care providers go to the client's home, provide care, and then record the services they rendered, and the time it took to deliver them, in a time sheet that is provided as a paper sheet that gets filled out. There are also assisted living facilities, nursing homes, and other service agencies providing in depth medical services and long term care. Typically, assisted living providers run a facility that the ailing can come to and live in, whereby health care professionals are available around the clock to provide care and support to the ailing residents.

For instance, the ailing patient lives at the facility, such as 24/7, and even though care is provided to their residential clients, there is typically no time sheets that are submitted with respect thereto. Rather, the care being provided is at most accounted for when invoiced, such as at the end of each month, whereby the assisted living facility merely indicates that the patient being cared for was present at the facility, services were provided, and the patient was cared for during the duration of that month. The benefit of such a system is that it is simple for record keeping and straight forward to transmit and receive payment thereof, because a detailed accounting of the services provided need not be tracked. However, this system is inefficient and is difficult to manage and track services being provided to ensure the quality of healthcare remains high.

There is currently a paucity of systems for tracking the care that care professionals provide to their ailing patients at these facilities, such as on an hourly and daily basis. Accordingly, a benefit of the devices, systems, and methods of using the same provided herein is the digitization, automation, and systemization of the entire processing of health care provision, such as at one or more, e.g., all, of the distributed care providers, home care agencies, assisted living facilities, VA/Medicare, and the like, as well as for insurance providers and/or other third party obligators. Regardless of the type of care giving facility, a number of doctors, physician's assistants, nurses, psychologists, paramedics, EMTs, and/or other healthcare providers and/or caregivers, and/or the like will be present to provide a wide variety of care and/or treatments to their client patients, including health care assessments, medicinal administrations, and treatments.

For example, a typical intake procedure would include an interview of the patient and/or a visit to the home of the client or treatment center, where information about the patient, their health status, conditions, complaints, ailments, medicines, and any other concerns of the patient to be treated, as well as to discuss the caregiving process. Particularly, one or more of these measures may be administered to a new client and/or patient such as in the process of making an evaluation and/or assessment of the client so as to determine their general health status and/or the needs they have with respect thereto. More particularly, as indicated, the caregiver can be any provider of any care that is sufficient to make a claim upon a third party obligator for treatment. In many instances, the health care provider may be a nurse or other assistant, such as an intake nurse, who is trained to conduct patient assessments and/or to provide care to the patients. In various embodiments, the assessor and/or caregiver are the same person, in various embodiments, these functions are performed by separate individuals.

In particular embodiments, the intake interview may be an electronic, intuitive interview generated and presented to the patient and/or healthcare professional, such as via a display of a client computing device of the system. The present system and methods are extremely useful, because in either instance, the nurse, or other health care provider, may make an initial assessment, via the interview, which may be performed in a manner, such as with guidance from the system, so as to align the assessment parameters with the payor required parameters for treatment and reimbursement. For example, a specific benefit of the devices and systems presented herein, as described below, are particularly useful in performing assessments of patients.

Specifically, in various embodiments, the system may be configured to present an online assessment interview that walks the patient, nurse, and/or other assessor through the questions generated by the system and/or otherwise to be elicited from the subject, and/or the procedures to be performed so as to generate an assessment that is from its initial origins adapted for being acceptable by the third party obligators of the system. Particularly, the questions can be designed and formatted by the system, or an operator thereof, such as based on the analytics run by the system, such as on the collection of data, specifically, treatment and/or policy data that was previously employed effectively in the past so as to receive reimbursement.

For instance, in various instances, provided herein is a client computing device that may be employed in generating and/or presenting an interview to a user of the system, such as a patient and/or healthcare provider who is seeking coverage for a proposed treatment. In such an instance, the client computing device includes a display that is configured for displaying a graphical user interface to an individual, e.g., a patient or healthcare provider, using the client computing device. The graphical user interface may be configured for generating a first interactive dashboard for presentation via the display, such as where the first interactive dashboard is adapted for presenting a claims interview to the first individual, and for receiving responses thereto from the first individual. In particular instances, the claims interview pertains to a treatment proposed by a healthcare provider to be administered to a patient in order to treat one or more conditions thereof. The results of the interview may then be employed so as to produce the patient data packet, which may then be transmitted by the client computing device, via a communications module, to a suitably configured server of the system, such as for consideration and analysis thereof.

Particularly, in various instances, the system include a computing device, such as a server system, that is configured for generating a patient interview, such as for presentation at a display at the graphical user interface, such as at a second computing device, via the interactive dashboard. In various instances, the interview may be an intuitive client interview that includes one or more interrogatories. Such interrogatories may be configured for eliciting one or more responses from the individual, such as where the one or more responses may be used to determine one or more personal characteristics and/or conditions of the individual. Likewise, the second computing device may be configured for receiving user comments in response to the generated interview, via the interactive dashboard, and transmitting those responses to the first computing device through the network connection. The received responses may then be for creating the individualistic characteristic and/or condition profile for the individual.

Once the individualistic characteristic and condition profile has been generated, it may be employed for generating a personalized condition search query, which query may be used for accessing the one or more searchable libraries so as to produce one or more identified characteristic conditions that may be pertinent to the individual. For example, the one or more identified characteristic conditions may be employed in generating a personalized treatment query. The personalized treatment query, in turn, may be used for accessing the one or more searchable libraries so as to identify one or more treatments that may be applicable for treating the one or more identified characteristic conditions pertinent to the individual.

Particularly, the individual characteristic and condition profile may be used to search a database of potential treatment agents and/or methodologies that are useful for treating conditions. The results of the treatment and methodological search may be a proposed treatment regime that may be used to treat one or more conditions of a patient. Accordingly, together the condition profile and the proposed treatment regime may be employed for generating a further search of one or more repositories containing terms of the patient's obligation agreement so as to determine whether one or more of the identified conditions and/or treatments will be covered by one or more of the terms of the obligation agreement. Together these data may be employed, along with one or more assessments, in generating the patient treatment data packet.

The interviews and/or assessments are useful, in part, because they may be used to set the parameters by which the healthcare professional will treat the client, e.g., patient, such as by providing care thereto, where the care to be given is defined by the parameters of the identified conditions and/or the terms of the insurance policy, and the like, as evaluated and determined by the system. Additionally, as it is the healthcare provider that sees to the needs of the client on a regular, such as a daily or weekly basis, and as such the system may also be configured for receiving input form the healthcare provider so as to determine whether the treatments suggested by the system, and to be covered by the insurance policy, are appropriate. If so, then a treatment plan and/or start of patient care packet can be generated, e.g., autonomously by the system or a user thereof, and if not, then the procedures in question may be flagged for follow up with the insurance company or other third party obligator so as to determine if an exception can be made, so as to provide the client a treatment that would not otherwise be covered by the system. Appropriate rules, statutes, or laws from a respective library may also be referenced so as to determine the appropriateness of accepting or rejecting the claims.

Accordingly, together the assessment, intake documents, plan of treatment, and/or other relevant treatment documents may collectively form a start of care packet that can be entered directly into the system or may be uploaded there into. Particularly, all of this data may be entered into the system, so as to build up a patient profile and/or a proposed patient treatment packet, which will allow the system to track the patient throughout the caregiving process, as well as to account for the types and times of treatments being rendered to them by a caregiver, as described in greater detail below. The health care professionals will then provide treatment to the patient or client, in accordance with the treatment plan, the system will keep track of the times, dates, and types of treatments that are rendered by the healthcare professionals, and they will be compensated by the health care company for their work. The healthcare company will then seek reimbursement, in the form of a claim submitted via the system, from the system administrator, who based on an evaluation made by the system of the supporting documents, will then pay out on the claim, pursuant to the client's health insurance, and/or will submit the claim to the insurance provider on behalf of the healthcare company and/or client.

In order to bill and get paid by the insurance companies and/or other third party obligators, care agencies and providers need to follow a variety of procedures by which to obtain authorization in accordance with the policy coverage pursuant to payment. Each procedure can be used by the system so as to generate one or more rules that can then be stored in a database of the system, such as where the rules are categorized and stored in a rules library. Specifically, to begin service, the healthcare service provider and a patient, such as a patient having a valid insurance policy, or other third party obligation agreement, enter into an agreement or contract whereby the caregiver provides care to the patient, in exchange for giving the care provider the right to receive re-imbursement from the insurance company for the healthcare provider, e.g., based on the insurance policy.

In such instances, in employing the present system, one or both of the service provider, and/or the patient, may assign their rights in the claims to the system administrator, or other third party. The third party may then submit the claims to the insurance company so as to seek reimbursement thereof on behalf of the client and/or patient. In some instances, an insurance policy may not be in place, and in such instances, the patient may assign their rights to further obligate another party, such as a government agency, such as Medicaid, Medicare, the VA, other private duty obligator, private pay obligator, such as a credit or debit card provider, and the like.

Accordingly, in various embodiments, provided herein is a method, such as a computer implemented method, for evaluating a claim for re-imbursement from a third-party obligator. The method may include one or more of the following steps. For instance, the method may include receiving at a computing device of the system, e.g., a client computing device and/or a system server, a claim for reimbursement from a claimant, such as where the claim includes information characterizing one or more services proposed to be administered or having already been provided to the claimant, e.g., patient. In response to receiving the claim, the computing device, or other system user, may retrieve one or more rules from a rules database, e.g., a rules library, associated with the system server. In various instances, the rules database may include one or more libraries storing a plurality or rules and/or laws setting forth a set of requirements for receiving payment of the claim. For example, the one or more rules may include a policy of the third party obligator, a code, a statute, a regulation, a government law, and the like.

Additionally, the system may include the performance of a comparison operation, e.g., performed by a server or other client computing device of the system, whereby the retrieved rules may be compared to the characterizations of the one or more services to be, or having been provided, so as to determine if the information of the claim includes a deficiency. For example, it may be determined by the system that the information of the claim includes a deficiency such as where the treatment proposed to be provided does not correspond to one or more of the rules and/or does not correspond to one or more of the terms of the agreement. Where a deficiency is determined, one or more corrective procedures may be implemented, so as to flag and/or otherwise retrieve the necessary information for correcting the deficiency.

Particularly, when it is determined that a least one deficiency exist, the system server provides an indication that a deficiency in the information is present, and/or may then determine the character of the deficiency and/or the identity of the deficient information whereby a corrective measure may be taken or suggested by the system. For instance, where a deficiency is present, the methods may include retrieving from an associated database the deficient information in response to the indication, so as to produce an updated claim, the updated claim having the deficiency resolved.

More particularly, a client computing device and/or server of the system may be provided wherein the computing device may be configured for determining if there is a deficiency of information in the patient data and/or claims packet, such as one or more pieces of missing or inaccurate information of the claim submittal packet. As indicated, when a deficiency is determined, the computing device may then perform an identification operation so as to identify and locate the missing or inaccurate information. Specifically, the computing device, e.g., server may be configured for retrieving correct information from the one or more databases of the system, and in response thereto can revise the claim submission packet in view of the correct information so as to resolve the deficiency.

Once the deficiency has been corrected, the method may include generating, e.g., by a score generator of the system server, a score, the score representing a likelihood that the claim will be paid upon by the third-party obligator. Particularly, the method further includes determining if the score is above a set threshold, and when the score is above the threshold an authorization may be granted thereby authorizing the claim so as to produce an authorized claim. Once authorized, the method may further include generating and/or submitting the authorized claim, such as in a claims packet, to the third party obligator for approval. Further, the method may include determining, by the system server, a time limit by which the claim is to be paid, such as where the time limit is determined by the one or more of the rules. Further still, in various embodiments, the method may further include embedding metadata within the claim packet and/or one or more claims therein so as to track the various claims throughout the entire process.

Accordingly, in part, the system may be configured for receiving the data pertaining to the treatments proffered by the various health care providers to their clients, such as in the form of intake packages, assessments, time sheets, and the like, and from these data an invoice may be generated. As explained in greater below, the data and documents to be submitted to the insurance provider, such as the time sheets, electronic visit verification (EVV) data, and the like, may be generated and compiled by the system, such as via interaction with an online portal and/or an application running on a client computer. In various instances, certain of the documents, such as hand written or pre-formed time sheets, may be scanned or otherwise digitally imported into the system, such as with respect to EVV data, and the contents thereof recognized and parsed, such that the information therein can be used to auto-generate one or more claims for coverage of treatments offered to the clients, and may be used to populate the database.

Accordingly, the system may include an optical character recognition (OCR) device that is configured to read scanned documents, parse the data, such as from the time sheet, code and/or embed the relevant data, as well as to compile, aggregate, and/or summarize the data so as to generate an invoice therefrom, e.g., weekly, which invoice may then be submitted, with the supporting documentation, to the third party obligator by the system. In various embodiments, the system and its component parts are configured to integrate with and import documents electronically and/or directly from various different sources, such as different applied management systems (AMS), for instance, through an appropriately configured application processing interface (API). Hence, the system is capable of receiving submissions regardless of the source of electronic visit verification (EVV).

The system, therefore, is configured for receiving inputs of data, evaluating the data, as well as generating and submitting an invoice thereby, such as to a third party obligator for reimbursement. In various embodiments, the system is further configured for compiling entered data across time for a single client, as well as across patients and/or health care professionals at a single time, or multiple times, and the like. Likewise, the various claims and/or other data, e.g., from a selection of patients, or a selection of healthcare providers and/or agencies and insurance providers, may be collected, aggregated, and compiled around a number of different parameters, so as to determine one or more relevant factors, such as related to generated billing, invoicing, and/or one or more trends related thereto, as discussed herein.

Once the invoice is generated it may be evaluated by the system for approval. For instance, the various obligators, such as insurance companies, require particular procedures to be followed in order to reimburse the healthcare providers for the services provided. For example, a start of care needs to be provided, a standardized assessment needs to be made, a timeline of the condition is detailed, what treatments have been performed, what remediations have been rendered and/or suggested, electronic visit verification data, and the like. All of this information is taken and entered into the system, and is used to generate a care packet, which will then be used in order to seek reimbursement, e.g., on behalf of the patient, from the obligator, e.g., insurance company, such as when filling out and opening a claim so as to beginning the billing process. In various instances, the questions included on the assessments may be standardized, or customized, based on computer generation, so that it need not matter who or which organization performs the assessment so long as it is entered into the system.

A plan of care is also determined. The plan of care will be informed by and/or may mirror the assessment, will include a detailed description of the patient conditions, a plan of action including the type of care to be given so as to treat the conditions, or at least ameliorate them, and will set forth if and when home visits are to take place, on what days and for how many hours. This plan of care may typically be included in their start of care packet along with the assessment. A HIPPA form and a consent contract attesting to the patient's agreement of treatment and care from the homecare provider may also be included.

Particularly, as indicated, the agreement will include an assignment of benefits from the patient or client to be treated to the health care provider. More particularly, the healthcare provider, e.g., a homecare provider or health care facility, will typically require the client to assign their benefits under their healthcare insurance policy, or to otherwise obligate themselves or a third party to the healthcare provider, in exchange for the treatments and care to be provided to them by the healthcare provider. In this manner, the healthcare provider will provide care to the client, and will then bill the health insurance provider or third party obligator on behalf of the client.

Specifically, a health care company will obtain a signature of the client assigning their benefits from their insurance or other third party obligator policy over to the health care company, e.g., a power of attorney, such that the health care company assumes the role of the insured or obligee and can now collect and demand payment from the insurance company or obligator directly. Typically, when the insurance company pays on a claim, they will generally send a check or wire money to the care provider, but in such instance, these payments may take about 30, about 60, about 90, or more days to be tendered. However, the system overcomes this difficulty by expediting the process and bearing the risk of repayment by the insurance company so as to pay the healthcare agency and/or provider in a much more expeditious manner. Essentially, whoever has the assignment of benefits takes over the role of the client.

Accordingly, in this instance, the system administrator receives the assignment of benefits for the clients and/or the healthcare providing agency, and in exchange for this assignment, the system administrator pays the service provider upfront, usually at a discount rate, and then submits the billing to the insurance provider and collects the reimbursement. However, in order to get paid by or otherwise reimbursed by the insurance company and/or by some third party obligators, various procedures need to be filed, so as to ensure that the care being provided is covered by the health insurance policy or other agreement of the client with the third party obligator.

There are, however, various problems with how these processes are typically employed. For example, prior to the devices, systems, and methods disclosed herein, neither the health care provider, nor the insurance company, have an easy to employ, automated system for generating billing, transmitting the billing to the insurance provider, evaluating the billing by the insurance provider, and authorizing and making payment on the submitted bills, such as where one or more of these steps and/or processes may be automated, so as to be performed by the system automatically upon the occurrence of a precedent condition. Particularly, prior to the systems disclosed herein, there is no systematic manner by which the reimbursement submittal forms are formatted.

This has been especially problematic when there is little to no correspondence between the submittal forms, the insurance policy, and/or the metrics by which reimbursement is authorized, such as between the various healthcare providing agencies, healthcare providers, and third party obligators. There is likewise no manner by which this process may be tracked either from the client side, the provider side, or the insurer side of the process. Hence, there is no transparency in the overall process, as there is no centralized platform that allows the various participants to communicate with one another and/or to track claims throughout the process. There is, therefore, a need in the art for a mechanism whereby these problems are overcome.

For instance, a platform is needed so as to allow a systemization of communication and exchange. Particularly, a platform allowing access to clients, care workers, facilities, and obligators, such as insurance providers, to be able to log on and access the automatized and systemized system. In a manner such as this, described herein, one or more, e.g., all, of the participants in the process can track and monitor claims as they progress through the system, such as in real time.

More particularly, as described herein, the recited platform is useful because it will not only allow for the tracking of claims, but can also allow for the immediate payment of claims when it is determined that the claims have a sufficient probability of being paid on, such as on or shortly after entry into the system and/or submittal. This is possible in part because the system may be configured for expediting the process, creating transparency and uniformity, as well as creating more certainty as to what constitutes an appropriate submittal that is likely to be approved and paid on.

Accordingly, provided herein is a system that is configured to receive assignment of benefits, e.g., power of attorney or otherwise assignment of rights, from the client and/or healthcare providers, receive the start of care packet, insurance policy, the assessment, plan of care, timesheets evidencing care provided, and other pertinent data related to the conditions and treatments, and then seeks reimbursement from the insurance company, e.g., on behalf of the healthcare provider and/or their client. Once received by the system, these documents are scanned or otherwise electronically entered into the system, are parsed, compiled, and a reimbursement submittal is generated so as to be sent over to the insurance company, e.g., via electronic submittal. For example, the entered data and/or documents, such as from a scheduler and/or time and care tracking sub-system, they may be evaluated for correctness, such as against one or more parameters set forth in the insurance policy, e.g., parameters regulating and/or otherwise characterizing the reimbursement process.

In view of the above, therefore, in one aspect, provided herein is a system for evaluating and submitting a claim to a third-party obligator. In various embodiments, the system may include a first and a second client computing device, such as where each computing device has an interactive touchscreen display. In particular embodiments, the client computing devices may include a downloadable application that is configured to run, or otherwise direct, one or more operations of the client computing device. For instance, the application may be adapted for generating a graphical user interface at the display of the client computing device, such as where the graphical user interface is configured for one or more of entering, retrieving, evaluating, and manipulating data Specifically, in various embodiments, the first and second client computing devices may be configured for receiving patient identification information including one or more of an identity of the patient, a nature of the patient's health issues and/or problematic conditions, as well as the patient's third-party obligation agreement setting out one or more terms of treatment coverage. In particular embodiments, the first client computer may be configured for determining whether a particular proposed treatment by the healthcare provider should be covered by one or more terms of the patient's third-party obligation agreement. A treatment regime to be administered by the healthcare professional to the patient may also be determined, such as where the treatment regime may be adapted so as to comport with the terms of the third-party obligation agreement. A treatment schedule by which the healthcare provider is to provide one or more treatments to the patient may be generated so as to produce scheduling data. Based on this schedule of treatment data a time sheet for the treatments performed by the healthcare provider may be generated, which time sheet may be employed by the first client computer in the generation of the claim submittal packet.

In one particular iteration, the first client computing device may be made accessible to a healthcare provider, and may be configured for generating a claim submittal packet including one or more claims for reimbursement, based on the treatments having been administered to the patient. In such an instance, the second client computing device may be made accessible to the third party obligator, which itself can be adapted for evaluating one or more claims of the claim submittal packet and determining if one or more claims are sufficient so as to be authorized for reimbursement.

The system may also include one or more databases for storing the patient identification information, the patient third-party obligation agreement, setting forth one or more terms of the patient's healthcare claim coverage, and one or more rules. Each of these data points may form its own library and/or may compose one or more nodes in a suitably configured knowledge graph. In various instances, the one or more rules may be directed at facilitating the assessing and/or determining of whether the characterization of the treatment provided corresponds with the one or more conditions of the patient and/or terms of the obligation agreement.

A server system may also be included. In such an instance, the server system may be in communication with one or more of the first and second client computing devices as well as the database, such as via a network connection. In particular instances, the server system may have one or more processing engines, such as where at least one of the processing engines may be configured for receiving, e.g., from the first client computing device, the claim submittal packet, and another may be configured for scoring one or more claims of the claim submittal packet so as to produce one or more scored claims. A further processing engine may also be provided so as to transmit the one or more scored claims to the second client computing device for evaluation thereby.

As indicated, the system may be configured for generating a timesheet, such as from a previously system generated schedule of activity. In certain instances, a standardized timesheet may be produced, whereby the timesheet may be based on the requirements of the various insurance provider policies, and their rules governing claim coverage. However, in various instances, the system may receive service agency provided documents, e.g., time sheets, which may then be stored and employed by the system in the generation of invoices.

Particularly, the timesheets and other associated documents are useful because they contain the information, recognizable by the system, which may be used for generating one or more invoices for reimbursement. In such instances, the data contained within the timesheets may be verified and if all the required information for generating and/or authorizing a claim, which data may be pulled from the timesheet and/or other documents, analyzed for completeness and correctness, and may then be employed for use in generating the invoice. If the data is inaccurate or missing, the inaccuracy may be flagged for required data entry.

More particularly, where a document includes a missing data feature, the system, e.g., a suitably configured Artificial Intelligence (AI) module thereof, may be configured for searching a database of the system for previous data entries that match the data field requirement, in which case the system may auto populate the missing data field. However, if the missing data cannot be identified as being present within the system, then the system may flag the data requirement, and send out an alarm and/or message, such as an email message, requesting the entry of the required data and/or fields. Such data may include the name of the insurance provider, the insurance policy and its terms, the name of insured, the name of the health care professional, the diagnoses and prescription for care from a treating doctor, the tasks to be performed by the health care professional or care taker in treating the patient, the patients electronic medical records/personal health records (EMR/PHR) information, an identifier of the patient, and the like. A signature may also be required and searched for.

Accordingly, the data to be entered into the system may be an electronically entered form, such as provided at a graphical user interface of the system, or may be a form that is scanned and entered into the system. For instance, for each patient to be treated, a series of data fields and/or documents may be entered into the system, such as including the insurance policy, which data and/or documents can be entered and/or scanned into the system, and can then be word, sentence, and subject coded, and from which process the other documents of the system may be evaluated to ensure the necessary information required for reimbursement have been included.

Typically, the data to be entered and used to generate the data packet may include the insurance policy itself, or a summary of the same, such as the verification page of the policy and/or the terms of the policy as well as its limits and/or exclusions. This information generally includes what is covered by the policy, and the parameters by which the obligator or insurance company is willing to pay for covered claims, such as immediately without prior authorization. For example, such parameters set forth how much the obligator is willing to pay per hour per day per treatment, and the like, given the age and treatment required by the insured.

Particularly, once generated, e.g., via the first computing device and/or approved by the second computing device, the data packet may be transmitted to a server of the system. For instance, once generated and/or approved the data packet can be transferred to the server from the interactive dashboard. The patient data packet may be employed in the creation of an individualistic characteristic profile for the patient, such as where the individualistic characteristic profile includes a characterization of one or more conditions of the patient, one or more treatments proposed to be administered to the patient to alleviate the one or more conditions, and/or one or more terms of the obligation agreement determined to be pertinent to one or more of the conditions of the patient and the one or more conditions of the patient. As indicated, one or more costs for the proposed treatments to be administered may further be determined and associated therewith;

Particularly, the data once entered, along with the timesheet and the invoice, can make up a patient data packet, specifically, a claims packet, which packet can include one or more claims. The claim(s) of the claims packet sets forth the authorization for service record, the policy guidelines, the services and/or treatments provided, and an explanation as to how those treatments are mapped to, or otherwise are justified by the policy. Any adjustments outside of the regular routine may also be evaluated to determine if they were authorized, and/or if the service provider can be reimbursed for the treatments under the insurance policy. Likewise, if there is a discrepancy between the scheduler, the datasheets, and the invoices, the system itself may resolve the discrepancy, or it may flag it for operator intervention. Once an invoice having one or more claims has been compiled, e.g., from all of the data collected, one or more rules may be applied to the data, such as in forming and/or evaluating the invoice and/or its claims.

For instance, in various embodiments, the system may include a rules repository, such as a database that includes one or more rules, such as a plurality of sets of rules derived from one or more insurance policies or parameters related to patient coverage, from one or more third party obligators, such as rules from Medic Cal, Medic Aid, the VA, and the like. In various embodiments the third party obligator may be a private duty payor, whereas in other embodiments, the obligator may be a government agency.

Particularly, various governmental agencies, like the VA, and/or private institutions do not employ classical insurance polices, but have other mechanisms by which to provide and track coverage of its authorized patients. For example, even though the VA does not typically perform its functions pursuant to insurance policies, it does have a set of policies by which it determines what procedures for which treatments will be authorized, and therefore, covered. In such an instance, the system will assess for the presence of a predetermined authorization from the VA prior to allowing re-imbursement. However, once authorization has been issued, the treatments can be performed, and the system can authorize payment on the claim, if appropriate.

More particularly, in various embodiments, the third party obligator may be a government administrated agency, such as Veterans Affairs hospital, Medicare or Medicaid facility, or the like. In such an instance, as indicated, an insurance policy, e.g., a third party obligation agreement may not be present with respect to determining whether or not a condition and/or a treatment therefor will be covered. However, facilities like the VA, and other like government agencies, do have various policies and procedures that should be followed in order to seek approvals for various procedures to be authorized to be performed.

Consequently, the system may be configured for receiving the rules, the policies, procedures, and the like from such government run agencies, for receiving the federal and state laws, statutes, and directives from these governments, and generating a set of rules by which to evaluate the proposed healthcare procedures to be rendered to a patient, determining and evaluating the patient's conditions, and determining if their conditions meet the government established guidelines mandating treatment and if so determining a likelihood that the procedures will be mandated. If the conditions precedent for receiving approval are present the procedure should be approved, and where such conditions are not present, the procedure should be disapproved, and where disapproved, a reason for disapproval, e.g., which condition precedent was not present should be highlighted.

In this manner, the evaluation and decision to approval or disapprove may be a straight forward manner. Particularly, if a government authorization has been made and/or vetted, and/or approved, and/or adjudicated, then the parameters of that authorization may then be used to generate a set of rules that can then be used to approve or disapprove various conditions of the treatment to be provided based on whether or not the conditions of treatment accord with the parameters of the authorization. If they do, then a digitally produced from for reimbursement may be generated and submitted, e.g., to the government, such as via a clearing house, for reimbursement. If they do not, then one or more claims can be adjusted to appropriate levels, such as by cutting times and/or procedures that do not meet the parameters, while leaving those procedures and time that do meet the parameters alone. Once appropriately modified to accord with the parameters of the authorization, the digital claim submittal form can be generated, any required coding necessary to receiving approval may be autonomously entered into the form, the form may be submitted, and reimbursement made, such as on submittal.

However, where a disapproval is received, the disapproval can be run through the rules and laws database may be searched and compared to the reason, e.g., condition, for disapproval. If the disapproval does not accord with the rules, e.g., laws, then a flag may be generated, and a dispute can be generated and submitted to the agency on behalf of the healthcare facility and/or patient. In such a manner as this, the system may be configured to perform an internal adjudication of the appropriateness of the proposed procedures to assure they accord with the parameters of authorization of coverage, and where deemed appropriate, authorization may be rendered. Once treatment has been administered, the particulars of the administration may be run against various required coding for that reimbursement may be looked up, e.g., via a look up table, the appropriate coding can be mapped to the procedures administered, this data may be added to the form, and reimbursement therefore may be made. Where coverage is not deemed appropriate, such as where a condition is not present, authorization may be denied, and reimbursement can not be authorized.

Hence, in a manner such as this, seeking reimbursement for claims predicted to not be approved can be avoided. This further avoids overbilling and unnecessary adjudication. Where approval has been determined by the system, the system may generate its own proprietary form for reimbursement, and/or can search for, pull, fill out, and submit the government generated form, such as a digitally generated government approved reimbursement submitted form and/or invoice, such as in a process of dynamic form generation. Likewise, whether the reimbursement form is produced and filled out by the system itself, or by the healthcare provider, the system may be configured for performing a double checking of the form to ensure it has appropriately been filled out, and where data is deemed to be missing it may be flagged for user review, and/or a search for the missing data can be made and where identified can be inserted into the form prior to its final approval and submission for reimbursement. As indicated, a number of these and other submissions can be aggregated and submitted as a block, where desired, and hence, in certain instances, the system may be configured for acting as a clearing house for such submissions.

For instance, various of the rules to be applied by the system may be derived from and implemented in accordance with the limits of the insurance policies, or by the details of the authorizations of various government agencies, and the like. These details, limits, and authorizations define the rules by which a given insurance claim will be evaluated, such as where the limits, details, and the like, indicates what will be covered and under what conditions. For example, in various instances, the limits and details may authorize, and therefore, cover, certain procedures, but not others, such as based on the type of policy, such as where a cognitive impairment policy will cover a treatment of a mental deficiency, but may not cover a treatment for an appendectomy, and the like. Likewise, certain treatments for a covered illness, malady, disability, and the like, may be covered, while other treatments may not.

Hence, the indications of what will and will not be covered can be determined by an operator or autonomously by the system itself, and can be used to generate the rules by which the various claims can be evaluated. Further, in various embodiments, when a claim is expected to be rejected, the system may be configured to perform an analysis on what claims were actually paid on, despite the fact that one or more rules have indicated that it should not have been paid on, and if payment is made nonetheless, the system may be automatically updated to reflect this new data, and the weighting paradigm can be revised to reflect a greater possibility of similar claims being funded. Likewise, should a claim that has a higher probability of being paid on, but does not get paid, then the system may flag this unexpected result for further review and/or conflict resolution, and may likewise change the weighting paradigm of the rules to reflect this new data. If the conflict is resolved positively on behalf of the client, then this may also be accounted for.

In various embodiments, the rules can be particularized to the various third party obligator or other participants of the system, or may be a generalized set of rules derived from a statistical analysis of a plurality of the various insurance and/or other third party obligator parameters of the system. Specifically, in various instances, the system may be configured to apply the same rules regardless of payor types, or may apply rules that are specific to each payor type, or a mixture of the same. In any instance, a computing device of the system, e.g., a server, may be configured for retrieving from the memory, one or more rules that have been identified as being applicable to the patient's obligation agreement, conditions, and/or the treatment provided to the patient by the healthcare professional.

Once retrieved, the computing device may then apply those rules to the treatments provided by the healthcare professional to the patient in scoring the one or more claims of the claim submittal packet. Particularly, the server may be configured for evaluating one or more of the rules being applied to one or more claims, and may then determine if the one or more rules are appropriate and correct, or in need of being updated. If correct, then the rules may be applied, and the invoice generated. However, if the rules were inaccurate, e.g., due to a rule change or a change in a governing law or statute or other policy, then the server may attempt to flag the need of and/or retrieve one or more updated rules so as to replace, in the memory, the updated rules for the old rules.

Accordingly, once a claim has been generated and scored, e.g., based on the data entered above, an invoice may be produced, which invoice may then be submitted by the system for approval, and ultimately be submitted to the third party guarantor for reimbursement, as described below. At some point during the submittal process, the system may authorize payment of the claims to the health care provider, such as prior to reimbursement by the insurance company, but upon affirmation by the system. Hence, once entered into the system, a calculation can be made so as to determine if all of the necessary information has been collected and collated into the invoice, and to what extent it fulfills the requirements of the insurance provider so as to make an assessment of the likelihood of being paid out on, such that when a given level of likelihood is achieved then a more immediate payment on the claims can be authorized and initiated by the system, such as prior to official submittal and/or approval by the third party obligator.

Specifically, at any time once the intake and/or start of care packet, including the assessment, time-sheet, and/or other supporting documents for treatments provided, have been entered into the system, evaluated, scored, and/or submitted to the insurance company or other third party obligator, payment may be authorized and rendered. Consequently, payment from the system to the health care provider and/or healthcare service agency may be authorized prior to or after submittal of the start of care and/or reimbursement packet, e.g., bill, to the third party obligator. More specifically, in some instances, payment to the health care provider may be made prior to or after an indication that the submittal has been submitted, accepted, and/or that reimbursement has been approved and will be made.

For example, in a first instance, payment by the system to the healthcare provider or facility may be authorized in a first instance, once the intake and/or start of care packet, including the invoice or time sheet, has been received and approved by the insurance company. However, in a second instance, once a first approval has been received, subsequent payments may be made more immediately after entry into the system, e.g., after evaluation or after submittal to the third party obligator. Hence, there may be two stages of the invoicing transaction, including a slower first stage of getting the client set up, treatment proposed and authorized by the third party obligator, and a more rapid stage where payments can be made on a regular basis based on one or more prior approvals.

So once a prior approval has been received, the system may conduct ongoing invoicing and authorizing ongoing payments more rapidly, such as on a weekly, bi-weekly, monthly basis, and the like. Particularly, once the start of care packet has been entered and/or compiled by the system, analyzed for completeness, corrected or embellished as necessary, it may be transmitted, or otherwise submitted to the third party obligator for approval thereby. For instance, once the scheduling data and time sheets have been entered, the data can be fact checked for accuracy by comparing the various different documents and data entered into the system one with the other, including a comparison between the insurance policy, the client or patient's medical records and/or history (EMR, PHR, and the like), the timesheet, the AMS, and other data related to the patient, the treatment, the care giver providing the treatments, the intake packet, the scheduling, invoices, and the like. More particularly, this comparison can be performed with respect to present or past documents and/or data, such as from prior time sheets, prior invoices, the intake packet, and the like, such as to make sure that the information between the different documents, such as between their AMS and the time sheets, matches, for example, prior to submission to the third party obligator.

As indicated above, if there are any discrepancies, such as between prior time sheets or invoices and a present one, these can be flagged so that the conflict may be resolved. Particularly, flagged data can be presented at a user interface, such as on a client computing device, or the system server can export a data packet to the local program running on the service provider system, such as to their AMS. Where a resolution is needed, the system can perform an auto-correct, or operator feedback can be elicited, such as where the scheduler indicates a treatment session of X hours, and the time sheet for the scheduled health care provider indicates that X+Y hours of treatment was rendered. In such instances, the flag could require verification from the care provider as to how many hours were actually spent rendering services to the client. In various instances, the system may generate a list of questions that can be presented to a system operator, or other third party, which questions instruct the system operator as to how to resolve the conflict, such as by identifying the conflicting or missing data, identifying the party involved, and what actions must be taken in order to correct the discrepancies and/or deficiencies in data, such as with respect to how the scheduler data or time sheet needs to be edited so as to reflect the accurate information.

Once the start of care and/or first reimbursement payment has been approved and/or received, then the subsequent submissions need only include the time sheet data and invoice. The time sheet, supporting documentation and data, and/or invoice perform the following functions. First, the invoice serves as a check for the timesheet as it reflects the time and tasks performed during the past billing period. Secondly, the invoice may cross reference and/or communicate with the AMS, EVV, and/or scheduler, or other health care provider software used to calendar, schedule, and track the various healthcare providers, their appointments, and the clients they see, as well as the services they provide thereto.

Particularly, the system may be configured to keep track of and monitor the who, why, when, where, and what of the care and/or treatments. For instance, who is being treated by whom, why they are being treated, and when, as well as where the appointment is and what services were provided and for how long. In certain instances, the software may be configured for logging all the activities the various healthcare providers in the agency perform, such as the list of services, treatments, medications, vitamins, supplements, and the like, to be delivered to the client or patient to be treated. The system can also map and track the locations of all clients and service providers so as to locate and provide directions to the service providers so as to be able to locate their appointments.

Likewise, the system may be configured for generating payroll for the caregivers, and thus, may be configured for generating and tracking caregiver appointments and activities for both generating payroll and for generating timesheets and invoices for reimbursement from the third party obligator. Hence, on one hand the system may be configured for running payroll based on the activities of the caregivers, and then also generating an invoice, such as for payment from the insurance company. And, as explained herein, based on the history of the service providing agency, the particular care provider and client, the system may authorize payment to the agency, such as upon receipt of the timesheet.

In various embodiments, the healthcare providers are scheduled to provide regular and recurrent services to the client, and thus, the scheduling system can be used to generate a time sheet and to auto-populate the same based on the recurring pattern of scheduling. The system may also be employed to generate an invoice along with the timesheet, which, once verified and evaluated, may be transmitted to the third party obligor, e.g., insurance company, for payment. The invoice may be based on the policy coverage parameters and the activities that were engaged in by the healthcare provider in administering aid or assistance to the client. As indicated, the scheduler may be employed to generate the time sheet and the invoice.

Accordingly, the system may be configured for performing all the processing required by the service providing agency, such as with respect to the management of their payroll, and/or the insurance company itself, such as with respect to their evaluation and authorization for payment on the invoices and claims. The system, therefore, may be configured so as to cross reference the time sheets, AMS and/or EVV data, and the insurance policy of the patients, as well as historic data so as to evaluate and determine them with respect for rendering payments and/or receiving reimbursements therefore. Particularly, on the service provider side, the system may be configured to receive and/or generate and/or correct the service provider timesheets, which can be evaluated, corrected, and submitted by the system or system operator for approval.

During the approval process, the invoice, its claims, and supporting documentation may be evaluated for approval. Upon approval via the website, once the data has been evaluated, the claim is effectively adjudicated. For instance, adjudication may be performed to evaluate and determine if a certain set of requirements are within the invoice and/or claims. This evaluation may look at and account for requirements that are co-dependent on others. Particularly, if it is determined that there is an indication of a given, e.g., cognitive, impairment that requires additional documentation to support a claim, such as an authenticating examination or other supporting documentation, then the system will look for and attach the supporting documentation, e.g., mental examination, to go with the claim. This is important because without the supporting documentation, the claim will likely be incomplete and, therefore, will likely be rejected and will not be paid.

The uploaded data is digitized, parsed, coded, and then compared against a set of rules that set forth the requirements that are needed to ensure that any given action item, e.g., claim, is accurate, fully substantiated, supported by necessary data, and in accordance with the policy limits. In many instances, the system may determine that the action items fall into a general category of not needing any further input. However, in some instances, where an action item is flagged for not meeting the general requirements for approval, they may fall within a category of needing a simple fix.

Such instances of a simple fix may require the system to provide a useful or necessary attachment in support of the timesheet or invoice, notifying an administrator of a need for a signature, a date or characterization of a treatment provided, and a time a task or intervention was initiated or completed. A simple fix may also require description of care tasks activities of daily living (ADL) that need to be provided, and the like. An indication of what ADLs the caregiver actually provided, such as the type of care or the things the caregiver does when he or she is with a client, may be supplemented by the system, such as by requiring further operator input, or by pulling data from prior submissions.

In other instances, where an action item does not meet the requirements for fitting in to a general category, but also cannot be easily corrected, the action items may be flagged for a more thorough processing, in which case the system may perform a more extensive database search to identify data for any missing category, or may indicate that a manual input is necessary. For instance, if a basic data field is missing, such as a client's or caregiver's name, identification designator, such as an electronic medical record indicator, a reimbursement code, and the like is missing, the system can fill in that data directly. However, in certain instances, the missing data goes beyond the basic requirements, such as missing time entry or signature, the system may identify the missing data, and may then send a query requesting that the missing data be entered. Accordingly, where the missing data relates to the need for special processing, such as where cross-referencing of data is required, such as for reimbursement, the system may signal the need for manual correction, or may search the database for the missing documentation so as to complete the cross-referencing.

For example, in various instances, compensation for certain treatment modalities require the submission of an additional or a subsequent form and/or approval. In a particular example, the client to be treated may have a particular condition, such as a cognitive or other such impairment, which condition may be indicated on their intake form as requiring extra validation or specialized treatment. In such an instance, an additional form, such as a qualification or evaluation, e.g., a mental evaluation, may be required in order to assure reimbursement for the treatment.

If there is an indicator of special treatment required, then the system may be configured for determining whether the information packet and/or timesheet, and/or invoice to be submitted to the insurance company includes all requisite additional forms. In particular instances, where a requisite form is included, the system may evaluate the thoroughness of the form to ensure that it includes the appropriate information so as to be approved. Where the form is determined to not include the requisite information, the system may search one or more databases for the missing information fields, and automatically populate the claim form with the missing information, or may signal the need for manual data entry. The system, therefore, is configured for performing real-time evaluation and/or adjudication.

Accordingly, the system may be configured for evaluating claims for various indicators of completeness and incompleteness, and when a claim has been determined to be incomplete, the system may then attempt to collect the necessary data to complete the form, or may signal that additional manual input is required. These basic elements of a claim are often derived from the entered timesheets. For instance, once a timesheet and/or invoice and/or supporting document has been entered or otherwise received in the system, the system may then evaluate the data to ensure that all the required fields have been entered so as to complete a claim and/or invoice.

The system, therefore, collects and evaluates the different elements to be submitted with regard to generating a claim, such as the basic requirements to build a claim, and then creates an invoice packet. Likewise, business rules are applied to the entered data, e.g., time sheets, etc., to ensure all the required fields to complete a claim and build an invoice have been completed. As an example, this process may include running one or more queries to ensure the claims data is complete, such as a query to determine the presence of necessary information, such as a signature, a query to determine that all of the time fields and treatments applied have been filled out, that the ADL is present, care giver information included, and the like. However, if data is missing, real-time correction may be implemented, whereby the necessary data may be retrieved and input, or if necessary, a signal for manual input may be generated. Specifically, if input is missing, and manual input is required, then the system may calendar a time by which to complete the entry, and a reminder may be set up. Once the missing information has been acquired and entered, and the claim validated, an invoice may be generated and may then be delivered to the insurance company for payment.

As described herein, the system may include a scoring engine that includes one or more processing elements that are configured for evaluating and scoring the entered data in accordance with a number of different parameters. Specifically, in various instances, the system is configured for receiving the start of care packet and supporting documents. These documents may include one or more of initial physician's or other health care provider's: assessments, evaluations, prescriptions, and the like, as well as the treatment plan, the insurance policy, the claims of the insurance policy, the time sheets, the schedule, other data from the AMS, and the like. Additionally, the system, e.g., via the scoring engine, may be configured for evaluating the entered data in view of a number of factors so as to generate a score for the data, such as a score for the invoice proposed to be submitted for reimbursement.

In particular instances, the scoring engine may be configured for authorizing a payment to be made on behalf of the patient, when the score is above a determined set-point level. For example, the score can be determined in a manner so as to reflect the likelihood of a reimbursement being made of one or more claims by a third party obligator. The factors by which the data may be evaluated may include one or more of: the nature of the malady, the nature of the assessments and evaluations, the characteristics of the patient, the prescribed protocols for treatment, the parameters of the insurance policy, the particulars of the health care providing methodologies, and the like.

During this process the evaluation engine may determine if there is a deficiency in one or more pieces of missing or inaccurate information of the claims packet. As indicated, and described in greater detail herein below, in particular instances, the scoring and/or evaluation engines may be implemented by an artificial intelligence module of the system. In such an instance, when a deficiency is determined, the artificial intelligence module may identify the missing or inaccurate information, and in response thereto the AI module, or other system component, may then retrieve correct information from the memory. The system may then revise the claims packet in view of the correct information so as to resolve the deficiency.

The scoring engine is an important element because the generated score can be used to determine a level and extent of the reimbursement payment to be made to health care providing agency and when. For instance, the payments may be made at a number of different levels such as based on a determination made by the factoring engine, as described herein below. Particularly, the higher the score on a claim and/or invoice, the higher the reimbursement may be and the more rapid the payment may be made. Likewise, the fee charged for providing the reimbursement and/or factoring services set forth herein can be based on the score, such as where the higher the score the lesser the fees, and likewise, the lower the score the higher the fees and the longer it may take to make the reimbursement, such as based on one or more predefined levels.

Further, in various embodiments, as explained in detail below, the system may be configured for communicating with the insurance provider, so as to thereby retrieve or otherwise receive an updated set of rules, as necessary. In this manner, it may be ensured that the most up to date evaluations are executed by the system. Consequently, the system may be configured for determining, generating, and scoring the insurance claims such as in substantially real time, thereby allowing for real time decision making. In one instance, this updating may be performed passively, such as by requesting the third party obligator to provide a copy of new rules once updated. However, in other instances, the updating may be active, such as where the system actively scans web-sites, as well as other publicly available online information, such as via a suitably configured web-crawler application.

In a manner such as this, the system may actively retrieve data regarding the policies and/or rules that given obligators employ in evaluating one or more claims of one or more insurance policies. Likewise, as explained below, the system may actively review the processes and results of the methods of seeking reimbursements, as described herein, so as to determine how the various rules of the system are being applied in actuality versus how they are supposed to be applied as published. Where there is a discrepancy between the two, the actual practices being employed by third party obligators, as observed by the system, can be formulated into new rules, which new rules can then be actively applied by the scoring engine in evaluating the claims of an insurance policy for submission to the third party obligator.

The system, therefore, is configured for receiving inputs, generating claims and/or invoices therefrom, and following and tracking the claims reimbursement process. Accordingly, the system is configured for allowing claims to be followed and tracked throughout the entire process. For instance, as described above, there may be a healthcare agency and/or healthcare provider login, a third party obligator or insurer login, and a client or patient login. Specifically, the system may include one or more of a server, a client computing device, an application, such as a downloadable application, running on the client computing device, and other system components.

In various embodiments, the system may include one or more of a web-based interface and a downloadable application, e.g., downloaded from a website associated with the server, which application running on a client computing device and/or a web-based interface, may serve as the gateway to the system. For instance, provided herein are methods for facilitating and/or tracking the treatments of patients, such as via the application and/or the web-based interface. In particular instances, provided herein are methods for assessing a client for treatment, scheduling, and tracking such treatments, for a number of different purposes, such as for generating and evaluating timesheets, invoices, supporting documents, and the like. Particularly, as disclosed herein these methods may be implemented by a downloadable application or other desktop interface that has been configured to be run on a client computing device, such as a desktop or mobile computing device, such as a handheld smart phone device.

In certain instances, the handheld mobile device may have a unique device identification code, such as for identifying and authenticating the user of the system, and may further have a geo-positioning functionality for locating the user in three-dimensional space. As explained herein below, this geo-locating functionality is useful for determining where a healthcare provider and/or a patient thereof is located, such as during treatments. Accordingly, the method includes generating, by the client computing device, e.g., by an application running on the client computing device or the web-page, an interactive user interface on a display of the device. The interactive user interface is configured for both presenting and receiving data, such as at the display of the computing device.

For example, the application may generate an interactive interview that may be displayed at the computing device. For instance, the interview may be a list of questions, where the questions are designed, and in some instances generated by the system, to assist the user, in this instance, a health care provider, in assessing the client for receiving treatments, such in accordance with their healthcare coverage, scheduling and tracking the treatment and coverage provided, and/or in generating a timesheet, billing statement, and/or invoice for the services provided. In various instances, the healthcare provider may be identified and their location verified by the RFID and/or the GPS of the mobile device. Particularly, in certain instances, a computing device of the system may include a project builder that is configured for providing a graphical user interface that is adapted for generating an interactive dashboard for presenting the interview to the patients and/or healthcare providers, and for receiving responses thereto. In one or more embodiments, the project builder is configured for employing the responses to the interrogatories to build the individualistic characteristic profile for individuals, which individualistic characteristic profile may be used to populate a personal characteristics library for the individual. Likewise, the project builder may be configured for employing the individualistic characteristic profile so as to generate a personalized condition search query, which in turn, may be used to search the structured database. In certain embodiments, the responses to a previous set of interrogatories is employed in determining which interrogatories will be included in a subsequent set of interrogatories. In particular instances, the intuitive client interview may include a series of sets of interrogatories, such as where each set of a series may include a number of interrogatories that are determined by the system to elicit in depth characteristics of one or more patients with respect to one or more of their physiology, biology, neurology, psychology, environment, emotionality, thought patterns, personality, health, wellness, and the like.

In response to the questions, the healthcare provider, or other user, may enter the answers thereto, and in some instance, the answers may be recorded and/or entered real time. The answers, along with the RFID and/or geolocation data, may then be transmitted, such as over a communications network, so as to be received by the system server. The application and/or server may then authenticate the user and/or patient, their location, and the treatments being provided. Specifically, authentication of the therapy provider and/or client may be made through the application, such as via user entry, as well as by the server through the received RFID and geolocation data, such as where the geolocation data locates the computing device within a determined geographical region. Likewise, the data, including the geolocation data, may be time-stamped so as to verify the time and place of data entry and/or transfer, such as with respect to the therapy being rendered.

Once the transmitted data has been received by the server, the server can then verify the healthcare provider, the client, and can verify if, when, and where the proposed treatment of the client has been provided by the healthcare provider, and can then determine if the proposed treatment is likely to be covered. If covered, the proposed treatment may be authorized, which authorization may be communicated to the provider, such as prior to treatment, and thus, treatment can be rendered. If not covered, the system may flag to the provider that the proposed treatment is not authorized, and/or may send a request to the insurance provider that they extend the clients coverage so as to include the proposed treatment.

If an extension is not made, then the healthcare provider can make alternative provisions, and/or render the treatment as desired, but knowing it may not be covered. If an extension is granted, then the treatment may be tracked and the policy parameters updated. Such verification can be performed by the system comparing the providers proposed plan of treatment with the insurance policy guidelines and verifying if the treatments fall within the policy's limits. In any instance, once authenticated and authorized, the treatments being provided, as well as the timing and participants thereof, may be tracked, and submitted to the invoice generation module such as for the generation of a time-sheet and accompanying invoice.

Particularly, the system may include one or more client computing devices that present a graphical user interface through which one or more of a healthcare agency, insurer, and/or a health care client can login, authenticate themselves, and gain access to the various subsystems of the system. In a manner such as this, one or more users of the system may login and track the claims, and/or other documents through one or more processes of the system, such as through the reimbursement process. Accordingly, the system functions as the main hub and/or point of entry and facilitator for the commercial aspects for the provision of health care from the client, to the health care service agency, to the health care and/or insurance providers. Hence, the system is configured for adjudicating one or more claims against one or more predetermined business rules.

However, in some instances, one or more business rules may be outdated and therefore in need of change. This change may occur manually, or automatically. For instance, each insurance provider has a list of requirements that are required to be fulfilled in order to meet a claim. These requirements may be explicit, and clearly set forth in their guidelines, or may be practical, such as not explicitly set forth, but practically applied none the less. In various instances, various rules may be determined based on the results of dispute resolution and/or litigation. Accordingly, the system may be configured to query whether the currently applied rules are the most update rules, and when it is found that one or more rules are outdated, the system may revise the applied rules and/or signal that an update to the rules is required to be entered into the system, e.g., manually, prior to indicating that a given claim is complete.

Another feature of the system is that it is accessible by the healthcare providing facility, the heath care provider, the client being treated, and the insurance provider or other third party obligator. Specifically, in various instances, the system serves as healthcare provision portal for the healthcare providing agency, a scheduler and/or treatment portal for the healthcare provider, and an invoice portal for the insurance provider. Accordingly, the system may be configured to allow access to system components to one or more of the healthcare agency and provider, the patient receiving the treatments, and one or more employees of the insurance provider. For instance, as indicated above, in various embodiments, the system may be configured for facilitating and/or evaluating one or more assessments that are to be made, or have been made. For example, with respect to rendering an assessment, the doctor, physician's assistant, nurse, or other person doing the assessment can access the assessment questions and/or enter the patient's responses thereto directly into the system, such as via the desktop interface or downloadable application running on the client computing device.

Particularly, as indicated, the system may be configured to generate a list of questions to be asked by the assessor directly, or the system may implement a voice activation and/or recognition protocol, such that as the patient or client begins speaking the system records, recognizes, parses, and derives meaning from the clients answers to the posed questions. However, in various embodiments, not only may the system generate questions, the system may also ask the questions themselves. More particularly, the system may generate a user interface by which the questions may be presented at a display screen of the client computing device, whereby the healthcare provider can read off the questions to the client and record the answers thereto, so as to determine plan of care, such as a plan of care that corresponds to the limits of the insurance policy. In other instances, the questions can be transmitted to a patient verbally, such as via a voice generator and/or speaker device. For instance, from the answers received in response to the queries, the system identifies key words that characterize the patient's conditions, which words can be weighted, coded, and attributed to one or more maladies consistent with or otherwise covered by the insurance policy.

Likewise, as indicated, the desktop computing device and/or the downloadable application, through the user interface, can also function as a scheduler and time tracker. For example, the system server can act as a central hub connecting the client application running on the mobile device, or other client computing device, with the scheduler, activity tracker, and/or geolocation device, such as for tracking the appointments and activities of the various different users of the system, such as with respect to the providing and/or receiving of healthcare. Particularly, the system can track the movements and activities of the health care provider, such as via an endogenous GPS of the mobile device upon which the application is running, or through entry at the GUI by the healthcare provider.

In like manner, the system may also track the activities of the healthcare provider, such as in administering treatments to the client. For instance, the system, such as a client computing device thereof, e.g., a mobile telephone, may perform or otherwise record an electronic visit verification. In various instances, one or more photos or videos may be taken and/or entered into the system, which images may be used to authenticate and verify one or more parameters of the treatments being or to be rendered, such as to authenticate the time, location, participants, and methods of treatments being implemented. Such iterations are useful for a variety of different purposes, such as for fraud prevention. As indicated, the system may manually and/or automatically track and log the movements of the healthcare provider, and/or may require the healthcare provider and/or user to enter various information at the time of service, so as to track activity.

For instance, when the caregiver shows up to the location of service, they may be required to log into the system in a manner that the date, time, and location of the caregiver can be verified, and likewise, the client can log in on their side to authenticate that the caregiver has arrived and that care is being rendered. The same can occur when the caregiver leaves. Likewise, the system can indicate to the healthcare provider and/or patient the list of authorized treatments or activities to be rendered during that visit, such as in a representation of a checklist whereby when a given activity is performed it can be checked off the list. Hence, the system can instruct the caregiver as to what activities and/or activities of daily living (ADLs) that should be performed during that treatment session. Also, if a treatment was not performed, that can be notated and accounted for by the system.

Once a treatment has been provided, each of the care provider and the patient may verify the services provider through the application. For instance, each person can authenticate the service by selecting a box indicating the service rendered, such as by interacting with a toggle presented at the user interface. In some embodiments, a passcode, password, or other form of user identification may be entered to verify that the treatment provider and the client have each engaged in a treatment protocol. In further embodiments, the app may be configured to authenticate the user, e.g., of a mobile device, by employing the phones endogenous finger print or facial recognition scanners so as to both identify and verify the user. Specifically, along with a client and healthcare provider and agency login, an insurance provider login may also be provided, so as to allow an insurance provider agent, such as a claims evaluator and/or adjuster, who is tasked with reviewing and approving the submitted claims.

Hence, through a graphical user interface presented at the client computing device provided by the insurance company, a claim can be generated, submitted to a third party obligator, and a claims evaluator can be notified that a claim has been made. For instance, once a claim has been submitted and the evaluator notified, the evaluator can pull up the policy covering the subject client, and can further access the plan of care, the start of care packets, the treatments provided, the time sheets, and invoices, as well as any other justifications in support of the claim. Through this insurance provider portal, the claims evaluator has immediate access to all documents needed to authenticate, evaluate, and accept or reject a claim readily at their disposal. And where a claim is rejected, the claim can then be forwarded through the system to a supervisor for review, and a notification can also be sent to the system administrator so as to pull additional information and/or arguments that can be submitted to further substantiate why the claim should not be rejected. Consequently, the system is configured for expediting the entire reimbursement process making it more intuitive and easy to use, while making everything more efficient.

Part of the efficiency is due to the fact that prior to submittal of the care packet and invoice, the insurance provider understands that a thorough evaluation of the claims and their supporting documentation, such that the insurance provider need not evaluate the claims as stringently knowing that an evaluation has already performed by the system. In certain instances, along with the document submittal, a confidence score, determined by the system, as to how closely the invoice package coheres to the terms of the insurance policy can also be sent to the insurance provider, whereby with a score at one level, e.g., 80 or 85% or 90 or 95% or higher, less review by the insurance provider is necessary, whereas a score of below these limits, may be subjected to further review, and scores below 75% or 70% Or 65 or 60% may require substantive review. This scaled scoring system, including the score generator, is useful because it objectifies and makes uniform the scoring regime across claimants and across insurance providers making the whole process much more objective and reliable.

Likewise, with greater adoption of the system, the more uniform the claims can be come, which in turn means the more uniform the time sheets and start of care packets can become. And further, the more uniform the insurance policies can become. In this manner the entire process becomes more objective and reliable. For instance, in view of the artificial intelligence module of the system, as explained below, the system can review the various treatments being provided, the claims being made, the claims being accepted and those rejected, so as to better determine the types of products being offered by the insurance providers, such that those claims being proffered the most may be suggested to be included in the insurance policies with a greater rate and a lower cost, so as to make the insurance providers more competitive in the market place.

Particularly, the system may include an insurance policy and claims limitation repository for receiving, evaluating, parsing, and compiling the insurance policies from its claimants as well as the various insurance companies serviced by the system. The repository may also include claims paid on, and the reasons for payment, as well as claims not paid on, and the reasons why the claims have not been paid. As described in detail herein below, this repository may be accessed by the AI module, such as by a learning engine of the AI module, such as for determining one or more trends as described herein. This is useful when considering large numbers, e.g., hundreds, thousands, tens of thousands, hundreds of thousands, millions, and/or tens of millions of claims, which can be mined by the system for data, as disclosed herein.

Hence, even where the insurance policy of any individual covered by an insurance company is lost or becomes inaccessible, the system will maintain a copy of the policy and its limitations within the policy repository. This is also useful when forming collections or blocks of policies, such as for forming derivatives, swaps, and/or other financial instruments, which could include both old and/or newly formed policies. In certain instances, the insurance provider can upload their policies into the database, and the covered clients can further upload their policies, the system can evaluate them, and where there is a discrepancy between the two a conflict can be flagged for further review and resolution.

In other instances, the insurance company can provide access of the system to their own database of insurance policies, rules, procedures, governing regulations, and the like, such as through a suitably configured API. In any of these instances, this is useful for authenticating that the client to be treated has a valid insurance policy, and/or to flag discrepancies where it appears that the client has an insurance policy but the insurance provider does not evidence the same. Likewise, where there is a conflict between the rules and procedures of the insurance provider with those implemented by the system, the system can auto-correct to adopt the insurance provider's rules. Or in various instances, the system can generate a conflict, such as where the insurance provider's rules, policies, or determined practices conflict a state or nationwide regulation, such as to the detriment of the insured.

This greatly expedites the start of care packet, timesheets, and invoices, as well as the payments thereof, such that as immediately as an invoice is evaluated and approved a payment may be rendered, such as via issuing of a check or ACH or wire transfer, and the like. Particularly, in a manner such as this, one or more portions, such as the billing and/or payment portions, of the system can be fully or at least partially automated. Where there is a conflict, an escalation may be flagged, and a dispute generated.

A unique functioning of the system is the development of applicable rules, as well as the application of those rules to a proposed claim, which once appropriately applied and adhered to can be used to generate an invoice packet that can then be sent to an insurance provider with the expectation of receiving payment thereof. Particularly, once the applicable rules have been identified and selected from any of a number of potentially applicable rules, the rules may be applied to the various claims, e.g., from a timesheet and/or invoice, in such a manner that a confidence score may be applied to the claim, where the confidence score is an indication of the likelihood that an invoice packet will be approved and paid. Where the confidence score is low, one or more elements of the invoice packet may be subjected to further processing whereby the claim can be strengthened such as by the input of missing and/or of additional data.

For instance, where an invoice packet has a lower score, a justification can be made whereby additional information in support of the claim may be made, such as where the justification may be any element that can be included along with a claim that justifies its approval, even despite it having a low score. For example, a justification may be a legal or statistical analysis based on a competent court's or agency's rulings, or statistical equivalency between this claim set and those previously approved, which justifies the approval and payment of the present claim. Consequently, the system can be configured for not simply generating a claim, but providing reasons so as to pre-empt the claim's rejection by the third party obligator, and/or to provides the means and/or justification for the filing of a dispute between the insured and/or the health care services agency and the insurance company.

In various instances, these reasons may be set forth in a system generated cover letter to accompany the start of care and/or invoice packet to be submitted to the insurance company. Likewise, where a dispute is to be filed, the nature of the arguments to be made and their relative strength can be determined by the system, so as to indicate how forceful an argument should be made and/or otherwise pursued, the result of which can be a scale of potential responses with an increasing level of demand strength. However, where an invoice packet that has been submitted for payment is rejected, the packet can be re-evaluated. For instance, the packet may be re-evaluated to determine if there was an error in data entry that resulted in the rejection, in which case, the missing data may be entered and the claim resubmitted. If, on the other hand, it is determined that no further data is required, and the claim has a relatively high confidence score, indicating that the invoice packet and claim should have been paid, then an escalation may be performed.

Particularly, where the rules have been applied in the appropriate manner to the claim, and there has been a high payout for such claims in the past, but for some reason this particular claim has not been approved, then an escalation can be provoked. An escalation can be any form of engagement that re-engages the insurance company requesting the reconsideration of a previously rejected claim. In various instances, the escalation may involve the submission of a legal or statistical analysis justifying why the claim of the invoice packet should have been approved. In particular instances, the escalation may include a pre-fabricated letter setting forth the reasons why approval was required or otherwise approvable, such as based on the rules. However, in other instances, where a first escalation was not successful, or a more particularized escalation is advisable, then the invoice packet may be flagged for individual analysis and escalation.

In addition to the score generator the system may include an inference module that may include an evaluation and/or factoring engine, wherein the evaluation engine includes one or more processing elements that are configured to evaluate and/or weigh a number of identified factors so as determine the optimal amount of pay to be given and at what time. For instance, as described above, the patient data packet may include a description of the characteristics and conditions of the patient as well as a list of one or more proposed treatments to be delivered, from which characteristics and/or conditions and/or treatments thereof, one or more rules may be generated. For example, such one or more rules may be based on a comparison with a database containing a plurality of other characteristics, conditions, and/or treatments, e.g., of others, that are relationally comparable to the conditions and/or proposed treatments of the data packet. Where those conditions and/or treatments have been covered a weighting of the relationship can be increased, +1, and when they have not been covered, the weighting can be decreased, e.g., −1.

Based on this comparison, incidences of previous coverages or lack thereof, the weighting of the relationship between the current conditions detailed in the data packet and the present incidence of claim coverage can either be increased or decreased respectively. This weighting can then be used by the system as a factor in determining an accurate probability that the claim will be covered. In like manner, the relationship between the proposed treatment in the data packet and other such treatments that have been administered to others and have been covered, or not been covered, as well as with respect to the various terms of the respective obligations, can be defined. Likewise, the instances between these various relationships may appropriately be weighted based on their instances, where positive relationships are increased in weight, and negative relationships are given a decrease in weight.

Accordingly, a structured database includes a rules library containing a plurality of rules, which rules may be used in accordance with the above weighting steps so as to determine the likelihood that a claim will be covered. As indicated, in various embodiments, the plurality of rules within the library may be previously generated and/or determined by a law, a statute, a regulation, a government ordinance, a policy, a practice, a procedure, or a principle of a governing body and/or the third party obligator. In particular instances, one or more rules governing the obligations of the third party obligator may be compared with one or more conditions that are substantially common amongst one or more patients, and/or may be compared with one or more proposed treatments. Specifically, such a determination can be performed by applying at least one of the plurality of rules to one or more of the conditions of the patient, the proposed treatment to be administered to the patient, and/or the terms of the obligation agreement for the patient, and then comparing the same with respect to other patients in the same or similar circumstances, where the previous relationships from other patients can be used to inform the present relationships, such as by applying a weight thereto.

Particularly, in determining the likelihood that one or more procedures to be taken are covered by the obligation agreement, factors in the various analyzed and/or compared relationships supporting coverage may be weighed against factors not supporting coverage. More particularly, when at least one of the plurality of rules have been determined to coincide with the one or more conditions of one or more patients, and/or the treatments administered to the patients, then the factors supporting coverage are given more weight. Likewise, when at least one of the plurality of rules does not coincide with the one or more conditions of one or more patients, and/or the treatments administered, then the factors supporting coverage are is given more weight. And when at least one of the plurality of rules conflicts with one or more of the terms of the obligation agreement, then the factors supporting coverage may be given more weight. Hence, because of the rules based system, it can largely be determined quickly, e.g., moments after uploading, whether an invoice packet will be approved and a claim paid or not, such as based on a score determined by the scoring engine.

Consequently, in various embodiments, the various patients' characterizations and/or conditions, their proposed treatments, the terms of their respective obligation agreement, and the rules with respect thereto can all be fed into the structured database of the system and may be used to generate a knowledge graph. In such an instance, the knowledge graph may include a plurality of sets of data points, wherein the plurality of sets of data points include at least a first set, a second set, and a third set, etc., such as where the first set includes data points pertaining to the individualistic characteristic profile, the second set includes data points pertaining to the conditions, which conditions have been determined to affect individuals, and the third set includes data points pertaining to wellness agents that could be capable of affecting one or more of the conditions and a characteristic of the individualistic characteristic profile. In various instances, the knowledge graph may be structured into one or more libraries, such as where each library may be directed to a designated classification whereby each data point within the library includes a descriptor having a common core referent.

As indicated, the various data points in one or more libraries can be connected in a relational hierarchy that can be weighted, whereby for each positive relationship that is determined, an increased value may be added to a weighted scale, and for each negative relationship that is determined, a decreased value may be subtracted from the weighted scale. In various instances, the weighted scale may be related to one or both of the personal characteristics and the wellness goals of the individual, whereby those identified relationships that enhance the individual's personal characteristics or wellness goals are attributed a positive, increased value, and those identified relationships that impairs the individual's personal characteristics or wellness goals are attributed a negative, decreased value.

In particular instances, data points pertaining to one or more individualistic characteristic profiles may include a plurality of data points characterizing one or more of the physiology, biology, neurology, psychology, environment, emotionality, thought patterns, personality, health, and wellness of the individual. Further, data points pertaining to the conditions may include a plurality of data points that characterize one or more conditions, such as where the one or more conditions may be classified by type, where each data point of a type may characterizes an aspect of an underlying condition. Furthermore, data points pertaining to the wellness agents may include a plurality of data points that characterize one or more wellness agents, such as where the one or more wellness agents may be classified by type, where each data point of a type may characterize an aspect of a benefit or a harm associated with each respective wellness agent. Additionally, in various embodiments, one or more data points of the knowledge graph may be employed for feeding information into, or otherwise assisting, a factoring engine of the system running one or more queries.

For instance, the system may include a factoring engine, which factoring engine represents a great advancement in the field, because prior to the present system, a home care provider would have to submit their claim to the insurance company directly, and then would have to wait in the dark from 30 to 60 to 90 days or more, not knowing if their submitted claim would be approved or not. A further complication could come in situations where the claim was rejected for a mere technicality, such as a missing signature, wherein the claim would then have to be modified, e.g., the missing signature obtained, and then the claim would have to be re-submitted and a new waiting period of 30 to 60 to 90 days or more would begin. In such instances, 180 days could pass before the health care professional has been paid from the time the claim was first submitted.

The present real-time system, however, can make an adjudication decision much sooner, and in view of this decision a payout to the claimant can be made much sooner and with greater confidence, based on the system's appropriate application of the rules. For instance, if the system has determined based on the performance of the scoring and/or factoring engines that a particular claim and/or invoice has a high probability of being paid on, then the factoring engine can perform a determination so as to authorize a payment that is higher, rendered faster, and at a lower rate. Likewise, if the generated score is lower, then the factoring engine may determine a payment that is lower and/or made later than would be the case if the score were higher. Or the payment can be made quicker but at a higher service fee.

In some instances, the factoring engine may determine that no fee should be paid at all, such as where the score is too low. Particularly, the system may be configured so as to not only determine if a payment on a claims should be made, but when, and for how much, and at what time, and at what fee. In such an instance, the invoice can still be submitted, and one or more claims made, but the payment may be kept from being made until and to the extent that reimbursement is made from the insurance company. In either instance, the system can review the facts and determine the weight of each fact in support and not in support of reimbursement, and then weigh the collection of facts so at to determine the degree to which one or more claims on an invoice can be supported, and which arguments to make to the third party obligator in seeking reimbursement.

Accordingly, the system may be configured for bringing the monetary compensation to the forefront of the transaction, such as making a payout to the client prior to the claim being paid out by the insurance company, in some instances, for a discount. In this manner, the system can weight and discount a payout based on the likelihood of the claim being paid and/or accounting for the time factor. Hence, the system can be configured for receiving timesheets, schedules, and the like, and from such time sheets the system may generate an invoice along with a probability indicating whether and to what extent the invoice will be paid, and based on that extent the system may authorize the immediate payment on the claim, such as at 100%, at 95%, at 90%, at 85%, at 80%, at 75%, at 70%, at 50% at 25% and below and all percentages there between. In a manner such as this, the system can be configured for providing a health care receivable factoring service.

This payment may be scheduled to be made on the day, the week, or the month it was received, or any day in between and the like. The payment may be made by the system to the health care providing agency or to the health care provider themselves, depending on how the system is configured. As indicated, a discount factor may be applied to the payment to be made such as from about a 1% to a 20% rate or more, based on a consideration of a variety of factors. Once a payment amount has been determined and/or factored, or any time before or after then, an invoice can be generated and sent to the third party obligator, such as for fulfillment thereby.

For instance, the first client computing device, or the server itself, can transmit the claims packet to the third-party obligator at the second client computer, which receives or otherwise retrieves one or more of the claims submittal packet and the third-party obligator agreement, and may further access one or more of the rules associated therewith, such as by accessing the server over an internet network connection. In various embodiments, the second client computing device may access the scoring regime, or perform an independent scoring operation, such as where one or more of the data of the claims packet can be evaluated based on an application of one or more rules from the third-party obligation agreement to the one or more claims.

Based on the results of the analysis performed, the third party obligator can either approve or disapprove one or more claims of the claim packet, such as via engaging the dashboard interface of the second client computing device. Further, as indicated, one or more of the first and second client computers may be configured for allowing one or more of the claims to be tracked through the process of approval or disapproval, such as where the approval may be based on the scoring. Particularly, the server may be configured for receiving an approval on one or more claims from a first or second client computing device, and in response thereto, an authorization for reimbursement of one or more of the claims of the claim submittal packet. In various embodiments, the scoring may be performed by an AI module of the system, as explained below.

Another advantage of the system is in the identifying of trends. For instance, as the system is the central repository of the interactions between the health providing agencies and the third party obligators, and as such the system has access to and processes tens, hundreds, thousands, tens and hundreds of thousands, and even multiples of millions, and even hundreds of millions of claims. Consequently, the system is notified when a claim gets accepted or rejected and for what reasons.

As described below in greater detail with regard to the artificial intelligence, the system therefore tracks and learns from the invoices being submitted the manner in which various acknowledged rules are actually applied in practice, the time period by which various of the claims are paid, the reasons for payment or non-payment and the like. These and other such factors can be supplied to a learning engine of the artificial intelligence module, whereby one or more rules as applied in practice can be compared to the rules as published, and where a deviation is identified, the system's rules may be updated based on how they are implemented in practice, rather than how they are stated or published, such as by the insurance company and/or as published in their insurance policies. Particularly, the system may be configured for determining one or more trends and updating or otherwise changing system parameters based on the determined trends.

Specifically, as the system is a rules based system that functions as a clearing house for the payment of insurance claims, mediating between a plurality of health care providers and a multiplicity insurance companies, such as 10 or 20 or 30 or 50 or 100 or more insurance companies. The system is configured for being dynamic and is capable evaluating the rules to be applied so as to make the overall evaluation process more efficient. Particularly, the system may evaluate the overall processes being run by the system against one or more characteristics so as to determine if one or more trends can be identified whereby a change in the rules may result in a greater efficiency being observed with respect to the observed trends and/or one or more operations of the system. For example, where a rule has become outdated, and the system flags a discrepancy between an expected or predicted result and an observed result, such as by a rule no longer being followed or a new rule being required, the system can automatically modify one or more of the set of rules being applied in the process in a manner so as to accommodate the new practices, or the system may flag the instance for manual review.

Particularly, a computing device such as a server of the system may be configured to include, or may otherwise be associated with, an artificial intelligence module. In various embodiments, the artificial intelligence module may include a machine learning component and an inference engine component. For instance, the machine learning engine may be configured for receiving the individualistic characteristic profile for one or more individuals, accessing the personal characteristics library for the individuals, and/or determining one or more personal conditions for each individual. Likewise, the machine learning (ML) engine may receive information related to one or more treatments that are known or have been determined to be related to the characteristics and/or conditions of the individual's.

Further, the ML engine may also receive one or more terms that are expected to be related to the characteristics, conditions, and treatments. Additionally, one or more rules may then be identified and be applied by the ML module to define one or more potential relationships between one or more, e.g., all, of these data points, which relationships may be used to make one or more predictions, such as with regard to determining one or more claims and further determining a likelihood that the one or more claims will be approved and to what extent they will be reimbursed. These determinations and/or predictions may then be tested by the ML module so as to better evaluate the rules of the system, and consequently, to make better determinations of which claims will be approved.

In such an instance, the ML and/or the inference engine may be configured for generating one or more correlations pertaining to one or more data points within the personal characteristics library, a conditions library, a wellness agent library, and/or a treatment library to generate the individualized wellness and/or treatment composition formula for the individual. For instance, the machine learning component may be configured for generating and/or receiving search results from one or more of a personalized characteristics and/or conditions and/or treatments search queries, and modifying the weighting of one or more relationships and/or associated data points within the structured database in response to receipt of the search results. Particularly, the machine learning component may be configured for receiving results from a first set of a series of interrogatories, and based on the received results thereof selecting a number of interrogatories from a library of interrogatories for inclusion in the generation of a second set of the series of interrogatories that may be presented to a patient, healthcare provider, and/or third party obligator that can then be used to produce a claim and/or an approval thereof. In various instance, the recited interviews may be an interactive, intuitive interview that may be administered as an iterative process whereby the machine learning component structures the interrogatories to be included in the sets of interrogatories to be administered.

More particularly, as described herein below in greater detail, the system may include an artificial intelligence (AI) module that reviews one or more data points forming one or more datasets that may be derived by the system to make predictions as to outcomes, and can then modify various rules of the system so as to more efficiently achieve predicted outcome. For example, if the payment time from an insurance company increases from 30 days to 45 days, the system can flag this instance, and automatically perform an analysis of the process to determine if there is a discernable reason for the change in payment timing, and can adjust the rules in a predictable manner to see if by implementing a change in the rules will result in a decrease in the time period for payment. Likewise, the system may identify a trend, such as where an insurance company stops making full payments on a claim, such as only paying for 4 hours of treatment where previously they paid for 6, and in identifying the trend, the system can identify that a change in the rules is necessary to account for the new practice, so as to not pay the claimant for 6 hours where it is now known that the insurance company will only pay for 4.

In such an instance, the system may generate a flag that indicates an inquiry should be made of the insurance company so as to determine why a change in the practices has occurred, and/or to hold the insurance company accountable for following their own rules, such as by provoking a dispute on the payment of the claim as not being in accordance with their states or published policies. Likewise, based on these new practices, the system may update its rules so as to reflect the new "conflicted" practices, and thus the mechanisms for determining scoring and factoring may be updated to reflect the new practices, such as until conformity with the published rules is determined, and/or the insurance company updates its rules to reflect its new practices in reimbursement. In addition, these procedures may also be implemented in similar manner if there is a change in the law, a regulation, a local ordinance, a court ruling, and the like, such as where there is a change in a law or regulation concerning the health care providers, the insurance company, or other third party obligator, or concerning the manner by which invoices are compiled and rendered, evaluated, and/or determined to be payable, or disputed such as where there is lack or a diminution in what was requested to be paid.

Accordingly, with respect to the artificial intelligence part of the system, in one aspect, with respect to the artificial intelligence module, in one aspect, a cloud accessible artificial intelligence module is provided. The AI module may be configured for being communicably and operably coupled to one or more of the other components of a processing facility, e.g., processing pipeline, disclosed herein. For instance, the AI module may work closely with a suitably configured workflow management system of the system so as to efficiently direct and/or control the various processes of the system disclosed herein. Accordingly, provided herein, is an AI module that is configured for acting as an interface between one or more characteristics of an individual, e.g., an individual having a third party obligation agreement, and one or more desired goals, e.g., therapeutic goals, of the individual, in addition to one or more factors, e.g., treatments, that will help that individual reach those goals, such as where the goal may be to receive one or more therapeutic treatments to treat one or more health related conditions, where the treatments administered are covered by the third party obligation agreement.

For instance, in various instances, the system may be configured for receiving input data, e.g., individual characteristic and/or condition data, as well as obligation agreement data. Such as data may be entered into a graphical user interface of the system, which entry may be in response to one or more interrogatories presented as an interview to the individual. The results of the interview may be data that includes the individual's responses pertaining to various medical and/or physiological conditions, such as clinical and/or medical data, pertaining to the individual.

In such an instance, the system may include a workflow manager, whereby the workflow manager of the system may be configured for receiving and analyzing the input data, and other such data, and may further be configured for performing one or more analyses on the data so to determine one or more correlations there between, such as to build and configure the above referenced knowledge graph. For example, in various embodiments, the methods and/or systems herein disclosed may be adapted for correlating an individual's personal characteristic data, e.g., such as from patient data packet. Such data may include one or more assessments, such as the intake assessment, a personal health record (PHR), and/or electronic medical record (EMR), which data may be stored and compared with a database of proposed treatment data, and/or with a database dedicated to one or more obligation agreements, along with the terms included therewith.

Specifically, as described herein, the system may be configured for generating an interview, such as an interactive, intuitive interview, whereby the interview may include a number of interrogatories that are configured to elicit responses from a user with respect to their personal history, physiological or biological or medical background, psychology, and/or environment. In various embodiments, the system may prompt a user, e.g., patient and/or healthcare provider, to upload, e.g., via a secure, encrypted network connection, one or more personal records, such as a personal electronic health or medical record, genetic data, and the like. In certain embodiments, the system may be configured for generating or receiving genetic sequence data. In particular embodiments, the source of genetic data may be derived and/or received from public or private databases, such as from academic and/or commercial diagnostic laboratories. Accordingly, presented herein is a system for searching a database, such as a structured database that may be configured as one or more libraries, identifying one or more results fitting the search criteria, and correlating data, such as correlating condition data, e.g., biological or psychological health data, with proposed treatment data, and the like, and/or with one or more databases of obligations and/or terms thereof, which may then be further correlated with one or more rules databases.

As indicated above, in various embodiments, components of the system may include one or more of a server, having a processor, a database, such as a structured database, one or more sources for subject related data, a graphical user interface for generating and/or presenting one or more patient interviews, and the like. In particular embodiments, the system may be configured to encrypt data files as that data is uploaded, or otherwise entered into the system, so as to ensure the maintenance of privacy. The files, e.g., records and/or index files, may be transmitted from each source of generation or storage to a repository using any suitable transference protocol, and may be searchable, such as via a browser. The GUI may be configured for searching the plurality of files, such as via use of the one or more index files. The server may be a plurality of servers.

In various instances, the system may be configured for running a plurality of workflows, e.g., pertaining to a plurality of patients, and may, therefore, include a workflow manager for implementing one or more of the analyses described herein, which in some instances, can be implemented in a processing pipelined configuration. Accordingly, as disclosed herein, the system may not only be configured for receiving user data, e.g., condition and/or treatment data, but in various instances, the system may further be configured for correlating the received data with a database of stored condition and/or treatment data and/or obligation and/or rules data. For instance, the workflow manager (WMS) of the system may be configured for implementing one or more deterministic rule systems, so as to derive results data pursuant to its analysis of the personal characteristics and conditions, and/or treatment data, as well as obligation and rules data.

For example, in certain embodiments, the system may include a variety of different databases, which various databases of the system may be configured so as to have a relational architecture, which may further be adapted to include one or more constructions. These constructions may be represented by one or more table structures. A series of tables, for instance, may be employed by which correlations may be made by the WMS in an iterative fashion. Particularly, in various use models, a first correlation may be made with respect to an individual's name, characteristic, and/or entered condition data, which may be included in one or more tables. Another table may then be employed to correlate the subject's condition data with a database of proposed treatment data that is predicted to help, ameliorate, and/or improve the one or more of their conditions. Likewise, with the appropriate feedback entered into the system, a further table may also be included and used to correlate the progress of the individual with respect to treating their conditions, such as with respect to the alleviation of symptoms and/or diseases that may be troubling them, e.g., for which they have a third party obligation agreement.

A key may be used to correlate the tables, which key may be accessed in response to question prompt or command.

The key may be any common identifier, such as a name, a number, e.g., a social security number, tax identification number, employee number, a patient record locater, a phone number, and the like, by which one or more of the tables may be accessed, correlated, and/or a question answered. Without the key, it becomes more difficult to build correlations between the information in one table with that of another.

Accordingly, a key aspect of the present technology is a data structure for answering a query, wherein the data architecture may be structured and searched in response to a query. In a typical architecture the database may be a relational database, such as a Structured Query Language (SQL) database, which may be implemented via a relational database management system (WMS). For example, in one implementation, the SQL database may be a document based database, such as where one or more tables, e.g., look up tables (LUT), form a structure wherein data may be stored, searched, relations determined, and queries answered. Particularly, in various embodiments, a document or table based database may be presented, searched, and used to determine relationships from which answers to one or more queries may be determined. For instance, typically, SQL databases have a relational architecture.

These constructions may be represented by a table structure. A series of tables, for instance, may then be employed by which correlations may be made in an iterative fashion. For example, with respect to the proposed treatment analyses discussed herein, a first correlation may be made with respect to a subject's conditions and with respect to their proposed treatments and/or the terms of their obligation agreement. Another table may then be employed to correlate the individual's conditions with one or more treatments and/or one or more terms pertaining to their conditions and/or treatment.

Likewise, as indicated above, a further table may be used to correlate the progress of the individual towards meeting their treatment by improving their conditions, such as with respect to the alleviation of symptoms and/or the conditions themselves. The individual may select their own identifier, such as name, phone number, driver's license number, a social security number, tax identification number, personal record locator, and the like, which identifier may serve as a key that may be used to correlate the tables, which key may be accessed in response to question, prompt, or command. The key may be used so as to access, search, and correlate data from the one or more of the tables such as in response to a query or question entered by the user, or generated by the system.

A further data architecture that may be used to structure a database is a data tree, where various data elements may be stored in a compressed, but correlated fashion, and/or in a hash table, as described herein above. In certain instances, the database to be deployed by the system may have a graph based architecture, which database may be structured and used to determine the results for one or more queries. In various instances, the graph may be configured as a knowledge graph. Particularly, a knowledge graph architecture may be employed to structure the database, so as to enhance the performance of computational analyses executed using that database. In certain instances, the sophisticated algorithms disclosed herein, are adapted for structuring the infrastructure of a relational database so as to enable more efficient and accurate searching such as via performing graph based analyses, as well as for performing table or tree based analyses.

Consequently, in one aspect, a device, system, and methods of using the same to build a searchable, relational data structure, such as described herein, are provided. For instance, in one instance, the machines and methods disclosed herein may be employed so as to generate and/or otherwise collect data, such as for the evaluation of one of more claims pursuant to a third party obligation agreement. Specifically, the machines and methods disclosed herein may be used to generate a searchable data structure for storing that data in a relational architecture. In various instances, additional data may be generated or otherwise be transmitted into the system, such as via a suitably configured network connection and/or API, which data may also be configured for being stored in the relational data structure.

For instance, in another aspect of the disclosure, the system may include an artificial intelligence (AI) module that may be configured to provide a more comprehensive analysis on generated and/or provided data. For example, the AI module may be configured so as to implement one or more machine learning protocols on the data attained by the system that are devised to teach the AI module to perform one or more correlations, such as between various conditions affecting the health of the individual and/or one or more treatments that can be administered to a patient, e.g., a subject, having a condition in need of alleviation, such as a condition expected to be covered by the obligation agreement. Specifically, the AI module may be configured for receiving one or more inputs and may be adapted for building and structuring a database.

For instance, in a first step, data may be collected, cleaned, and then be prepared for analysis. In various embodiments, the data may be labeled and/or categorized, such as with respect to metadata. For example, a skimmer may be implemented for the purposes of structuring the database, such as for providing a relational structure to the database. And once the database is structured, it may then be populated with data, in accordance with determined or inferred relationships.

In certain instances, a machine learning protocol, as disclosed herein, may be employed so as to determine relationships between data points entered into the database. Such relationships may be determined based on known facts, and as such the learning may be supervised learning, e.g., such as where the data entered into the database is categorized in accordance with one or more categories and/or labels. Particularly, known factors may be used to label, categorize, and store data, which may be informed by the query being sought to be answered. Hence, knowing factors by which to label and categorize the data being stored makes building the storage architecture more efficient.

In other instances, the learning may be inferred, such as in an unsupervised learning. For instance, in certain instances, the data to be stored may not be known, relationships between the data may not have been determined, and the query to be answered may also not be identified, and in such instance, the system may be configured to finding answers to all of these questions. In such instances, the data to be stored is unsupervised, and as such, patterns in data to be stored and their relationships, such as commonalities between data points, may be determined, and once determined such patterns may then be used in forming the architecture that structures the data storage. For example, in various embodiments, the AI module may include programming directed at training the system to more rapidly, e.g., instantly, recognize how an output was achieved based on the type and characteristics of the input received. The system, therefore, may be configured for learning from the inputs it receives, and the results it outputs, so as to be able to draw correlations more rapidly and accurately based on the initial input of data received.

Typically, the input data may be of two general types. In a first instance, the data may be of a type where the output, e.g., the answer, is known. This type of data may be input into the system and used for training purposes. The second type of data may be data where the answer is unknown, and therefore, must be determined. This data may be any form of data. However, in various instances, this data may be data pertaining to a description of one or more conditions, such as describing one or more conditions a subject may be experiencing. This condition data may be analyzed such as to correlate the conditions, or one or more of their effects, with one or more proposed treatments that can be administered to improve the one or more conditions, and likewise, one or more of the above may further be compared to one or more claim terms and/or benefits.

Effect data, such as feedback data may then be elicited from the patient, healthcare provider, and/or third-party obligator with respect to what extent the administration of the treatments may be administered, the patient's conditions alleviated, and/or the treatments costs covered, improved the one or more conditions of the individual. These effects data may be used to enhance the AI module's ability to learn from the first type of input data, condition data, so as to better predict the outcome for the second kind of input data, inferred treatment and/or coverage data, so as to better correlate conditions with those agents that can affect those conditions, such as in a positive or negative manner.

Specifically, based on historical evidence, e.g., from a plurality of patients having a plurality of obligation agreements, the AI module may be configured to learn to predict outcomes based on previously observed data, such as with respect to various of the individual users of the system experiencing the same or similar conditions or affects from having ingested one or more wellness agents. More specifically, a wellness enhancement platform is presented herein, wherein the platform is configured to correlate descriptions of conditions, such as wellness or health conditions with data pertaining to various wellness agents. In such an instance, one or more user profiles may be generated for various of the users of the system, which user profiles may be generated by subjecting one or more of the users to an interview process designed to elicit answers pertaining to one or more of the user's wellness goals and/or conditions.

Particularly, in combining these two datasets, the AI module may be configured for determining the various interrelationships between them. Accordingly, at the heart of the AI platform may be a structured architecture, such as a graph based database, which may be configured for receiving data from a plurality of different sources, such as from user entered responses to the one or more interviews described herein, or other user entered data, and/or sources of information pertaining to the individual and/or their described conditions, wellness goals, and any type of other data useful in accordance with the systems and methods disclosed herein. As indicated, the system may be configured for employing the received data in one or more learning protocols, such as for machine learning.

For instance, machine learning takes place by training the system to instantly recognize how an output was achieved based on the type and characteristics of the input received. The present system is configured for learning from the inputs it receives and the results it outputs, so as to learn to draw correlations more rapidly and accurately based on the initial input of data received. The system, therefore, receives a first set of data wherein the outcome is known, and this data is employed by the system to generate one or more rules by which a result may be obtained, and once obtained compared to the known outcome.

Consequently, the system may be configured to train itself to better recognize correlations between data points within the database more accurately, e.g., with less false positives, and more efficiently, and to make predictive outcomes. In such a manner the machine learning algorithm may learn behaviors, determine accuracy, and may be used by the artificial intelligence module to analyze further sample sets with respect to answering one or more search queries, such as a query requiring the AI module to infer correlations between nodes or datasets. Hence, once the AI machine learns the behavior, the learned behavior may then be applied to a second type of data, such as an inference engine, that is used to answer one or more unknown variables.

The more the machine learns from the first type of input data, the better the inference engine becomes at predicting the outcome for the second kind of input data. Specifically, based on historical evidence, the artificial intelligence module may be configured to learn to predict outcomes based on previously observed data. With respect to the wellness goals, condition data, and/or characteristic data of the system, the present claims analysis platform is configured to correlate the conditions being experienced by an individual with the effects of the individual having received the one or more proposed treatments, e.g., based on the individual's reporting on the outcome. In such an instance, the self-reported conditions and treatments effects as well as the coverage profiles of subjects are assessed along with a description of the individualistic characteristic profiles and their third party obligations. Particularly, in order to combine these data, their interrelationships are determined.

Accordingly, in a first step, a graph database or knowledge graph may be constructed. For example, in this instance, the knowledge graph may be composed of three typical elements, which basically include a subject, a predicate, and an object, these may form nodes, and the relationship between the nodes must be determined. Any particular data point may be selected as a node, and nodes may vary based on the queries being performed. There are several different types of relationships that can be determined. For instance, relationships may be determined based on their effects, e.g., they are effect based; or they may be determined based on inferences, e.g., relationships that are unknown but determinable.

Particularly, each effect and/or relationship may be characterized by different properties or characteristics, which characteristics may be used to generate weights, probabilities, make assumptions, and the like. Such properties may be used to populate the knowledge graph with data points that may form the nodes of the graph. More particularly, to better determine causal and/or predictable outcomes the various different relationships may be weighted, such as based on the degree of certainty, number of commonalities, number of instances sharing the node, number of common relationships, and the like. In various embodiments, a schema may be formed, such as where the schema is an architecture that is used to give structure to the graph. Hence, the construction and implementation of a dynamic knowledge graph may be at the heart of the wellness analysis platform.

For example, with respect to constructing the knowledge graph, any particular data point may form a node. For instance, on one side of the graph a patient condition in need of treatment may form a node, and on the other side of the graph a set of proposed treatments may form another node. In between these two nodes may be a third node, e.g., a series of third nodes, such as one or more rules, including:

principles, procedures, practices, laws, statues, and the like. Additionally, in between these nodes are the relationships that may be determined.

Specifically, when building the knowledge graph, condition data input into the system, such as from an individual's responses to a set of interview questions, uploaded data, e.g., the client data packet, such as including: electronic medical or health records, family history, environment, psychological and/or medical conditions, etc. that may be encrypted and securely transferred electronically. One or more proposed treatment nodes may also be formed, whereby one or more treatments that are in some way related to the patient's conditions may be populated within the knowledge graph. Further, one or more terms of the obligation agreement may also be formed as one or more sets of nodes as well. Once these two or three sets of nodes have been established one or more queries may be input into the system, from the presence of which the relationship(s) between the two original nodes may be determined.

For instance, in one example, a first node may be represented by the conditions of a person or a population of people, and a second node may be represented by a treatment proposed to be administered to the patient for improvement of the condition. In such an instance, one or more third nodes may be input to the system and generated within the graph, such as where the third node may be one or more terms of the obligation agreement that mediates between the conditions of the patient and the proposed treatments for ameliorating those conditions. A series of relationships may then be determined by analyzing various points of connection between these three items.

Particularly, in a particular instance, one node may represent an individual's conditions, a second node may represent one or more proposed treatments, and a third node may represent one or more terms of the obligation agreement. Likewise, this process may be repeated for multiple individual's having the same or similar characteristics and/or experiencing the same or similar conditions, and/or having the same or similar obligation agreements. Hence, in a manner such as this, the correlation between individuals' conditions and the proposed treatments that affect those conditions may be determined.

Accordingly, a step in building a patient characteristic data packet graph is to define the anchor nodes, these represent the two bounding elements between which all the various commonalities are defined and explored. A further step is to define all the possible known correspondences between the two anchor nodes, which may be represented in the graph as a further node, such as a rules node. These known correspondences may be built around detailing the effects caused by and/or the characteristics of one node or the other. These may form the known and/or observable relationships between the nodes. From these known relationships, a second type of relationship may be explored and/or determined which relationships may be built on inferences. Further, to better determine causal and/or predictable outcomes the various different relationships may be weighted, such as based on the degree of certainty, number of commonalities, number of instances sharing the node, number of common relationships, and the like.

Hence, in various embodiments, the construction and implementation of a dynamic knowledge graph is at the heart of generating the patient characteristic and/or claim package, such as for submittal to the third party obligator. As indicated, the various processing platforms of the global system may be coupled together, so as to seamlessly transfer data between its various components. For instance, as indicated, the receiving and transferring of the responses to the interviews, e.g., results data, to the artificial intelligence module may be performed in a substantially seamless manner, such as via a hyper-interconnect.

Particularly, the AI module may be configured for receiving the interview results from the query generating engine, and for taking the results data and using it to generate one or more nodes, e.g., personalized to the individual, within the knowledge graph. Further, as indicated, the AI module may be configured for receiving input data from one or more other sources, such as from a medical office, a health care service provider, a research lab, a records storage facility, and the like, such as where the records include data pertaining to the physical, mental, and/or emotional well-being of one or more of the individual's so as to more fully develop the individualized nodes of the subject, and for taking that data and using it to generate one or more nodes within the knowledge graph. Furthermore, the system may further be configured for retrieving data about one or more treatments proposed to be administered to the patient so as to treat the patient's condition, which data once collected may be used to generate a further set of nodes within the knowledge graph.

More particularly, the system may retrieve pertinent condition and/or treatment data in any suitable manner, such as by eliciting interview responses from medical, healthcare, and/or research professionals regarding those conditions, and/or may include a skimmer or search engine that collects data, e.g., online data, that pertains to the various conditions and proposed treatments of the knowledge graph. Additionally, once the knowledge graph architecture has been constructed, it can continually be updated and grown by adding more and more pertinent data, from one or more individual's, into the knowledge structure, building more and more potential nodes and/or relationships. In such an instance, the bounding nodes may be of any combination of nodes, and as such, in certain instances, may be user selectable.

For instance, in various embodiments, the system may be configured for being accessible by a third party, such as by the individual themselves, the care providing practitioner overseeing the administration of the system, a third-party healthcare professional, or insurance provider, and the like. In such an instance, the user may access the AI module, e.g., via a suitably configured user interface, upload pertinent information into the system and/or determine the relevant nodes by which to bound an inquiry, e.g., by clicking on or drag and dropping them via the dashboard interface, and may formulate a relevant question to be answered by the AI module. Accordingly, the user may review and/or select the bounding nodes, and then allow the system to generate an appropriate knowledge map employing the selected nodes, and determine the relationships between the nodes, from which relationships various inquiries may be queried and answered, or at least be inferred, e.g., by the AI system.

For example, in one use model, a user may be a healthcare practitioner, psychologist, physician, or the like, who desires to know whether a certain condition that is affecting the individual, with respect to one or more characteristics thereof, may be ameliorated by one or more proposed treatment regimes. And likewise, the healthcare professional may utilize the system in order to confirm that the proposed treatment of the condition is covered by one or more terms of the obligation agreement. Consequently, the healthcare provider may upload the individual's detailed description of their conditions, which may be in the form of one or more electronic health and/or medical records, a description of the individual's health condition, and/or an interview administered to the patient, such as an intake interview.

Next, a review of the identified condition of the patient may be employed, e.g., by the system or a user thereof, so as to identify one or more treatments that can be used to treat, or at least ameliorate, one or more of the conditions. Likewise, one or more terms of the obligation agreement can also be parsed, identified, and applied to one or more of the conditions and treatment graphs so as to determine one or more covered claims. With this data the AI module may generate a suitable knowledge graph (and/or add to an already existing knowledge graph), from which knowledge graph the bounding nodes may be selected and various relationships between the nodes may be determined. Further, in various instances, the individual's characteristics and conditions and/or EMR and/or family medical history data may be correlated within the knowledge graph with the various proposed treatments that may be known or expected to help alleviate or enhance those conditions and/or the particular terms of the third obligation agreement, from these data points within the graph various relationships may be determined, inferences assessed, and predictions made.

Specifically, in various embodiments, an overseeing healthcare practitioner may administer and/or review one or more interviews with the individual and/or may perform one or more clinically relevant tests on the individual, and enter the data into the system so as to build out the individual's personal characteristics profile within the system, such as for developing a client intake and/or claims packet. This data may then be employed, e.g., by the wellness practitioner or the system itself, to define the characteristics affecting the individual and/or delineate one or more conditions that the individual may be experiencing, such as a condition that may be adversely affecting them. From these data one or more nodes within a knowledge graph characterizing that individual may be generated and one or more nodes representing one or more proposed treatments may be populated and be evaluated for formulating an individualized treatment regime to be administered to the individual at a predicted or otherwise determined dosage so as to help that individual meet their wellness goals. Further, these nodes may be counter-referenced with a third set of nodes that are generated from parsing the obligation agreement and feeding the terms into the knowledge graph to serve as second or third set of nodes therein.

Particularly, with this data the AI module may generate one or more suitable knowledge graphs (and/or add to an already existing knowledge graph), from which knowledge graph(s) the bounding nodes for the individual, their conditions, and one or more treatment protocols, may be selected and relationships between them determined. A workflow for determining one or more characteristics and/or conditions may be worked up, e.g., previously embedded within the system or entered into the system, a query may then be run, so as to identify a medical condition that may be related to, e.g., causing, the patients conditions. Likewise, another workflow may be engaged so as to determine one or more treatments that can be worked up, e.g., or be previously embedded within the system, such that a query may be run so as to identify one or more proposed treatments for the individual. A further workflow may be worked up so as to determine if one or both of the conditions being experienced by the patient, and the treatments being proffered to treat those conditions, are covered by a third party obligation agreement.

A predictive model may be initiated on the data to determine one or more relevant query results that are particular to the individual's personal characteristics with respect to one or more of the generated work ups. Accordingly, the present system may be configurable so as to account for the personal characteristics of an individual, both with respect to their physiology, biology, psychology, which may include genetically, e.g., from a genomic analyses performed for the individual, and/or phenotypically, e.g., from the individual's self-described feelings and/or experiences about one or more conditions they may be experiencing. Likewise, the system may include a large database of treatment regimes, and the characteristics that describe them, which treatments may be known to be beneficial in positively affecting one or more of the conditions. However, the included wellness agents may not heretofore be known to affect one or more conditions but may be predicted, based on an analysis performed by the system, to affect the condition, such as based on one or more inferences made by the system.

In any of these instances, these characteristic data may be uploaded into the system and may be populated into one or more knowledge graphs of the system, whereby various nodes may be identified and/or correlated from which data correlations and various relationships may be determined, inferences assessed, calculations performed, and predictions made and/or reported. For instance, in such a manner, this data, as well as any other relevant data, along with all properties relevant to a particular query to be analyzed, may be uploaded into the system and be used to form a constellation of nodes, which nodes may be employed to determine various relationships pertinent to the individual, such as by querying the system and allowing it to generate the appropriate connections from which an answer may be inferred. Once populated in a manner such as this, one or more queries may be run against the data so as to isolate various sub-profiles that may then be mined for relevant relationships and/or correlations.

Specifically, these characteristic data may then be employed by the AI module so as to determine one or more correlations and/or perform one or more calculations with respect thereto and thereby derive and propose a treatment thereof. Specifically the AI module determines a treatment regime to be administered, which treatment regime may include a determination of a procedure to be administered, a medicament to be dispensed, and/or a calculation of a proposed calendaring of administration and/or dosage. The results of the treatment and/or administration may also be entered into the system and tracked over the course of time.

For instance, in various embodiments, these results may be used to generate a collective knowledge graph of a plurality of individuals, and/or for each individual over a longer period of time, whereby pertinent data may be entered into the system. In such an instance, any relationships between the various data points may be determined by the AI module, such as relationships that are common between them, e.g., relationships between two or more characteristics in a subject, or between subjects, may then be determined. This may be done for a single subject or multiple subjects, e.g., forming a population of subjects.

More particularly, in one use model, a relationship between two properties, e.g., property A: an individual's experience of one or more conditions, and property B, one or more characteristics of a treatment that is proposed to be administered thereto that is in some way related to the individual's conditions. This relationship may be determined by the system, and then one or more terms of an obligation to cover one or more of the conditions by one or more of the treatments may be made. And this data for one patient can then be compared to other such data from a variety of patients in the same or similar circumstances, whereby one or more predictions may be made, such as for the purpose of making a prediction as to whether one or more future claims will be covered.

Specifically, a series of historic readings for each property, e.g., of a reading of a condition, may be entered into the system, e.g., such as from a plurality of patients, such as 10, 100, 1,000, 10,000 readings or more, whereby the machine learning platform of the system may analyze the readings, and/or determine one or more correlations and/or relationships between the two properties. Accordingly, if a given property, e.g., condition A, is entered into the system, and a second property, e.g., treatment B, is entered into the system, than a third condition, e.g., relationship C, such as whether an identified claim for coverage of the treatment, may be predicted. Particularly, where a prediction is to be made, a historical context may be generated, whereby previous instances of conditions A and B have resulted in a positive outcome C can then be used to weight and predict the outcome of a subsequent occurrence of conditions A and B leading to the positive outcome C, such as where output C may be inferred, taking the predictive weights between the two into account.

In such an instance, when evaluating the inputs with reference to properties A and B, a relationship between the two may be determined by the artificial intelligence processor, such that if given a new input for properties A and B, the determined relationship may then be used to predict what the outcome of property C will be, given that the two properties are in fact mathematically related. This machine learned relationship may, therefore, be employed to determine when the two or three properties are in alignment with one another, e.g., everything is functioning as it should, and may further be used to determine when things are not functioning in alignment, such as when the predicted outcome is not observed, and thus, is indicative of their being a problematic state, which may be flagged by the system. It is to be noted that the preceding applies to any given nodes that are in a mathematical relationship to one another, such as with respect to a multiplicity of subjects and/or a variety of conditions.

In certain instances, however, the relationship between two or more properties are not linear, but rather may be more complex. For instance, in certain embodiments, the artificial intelligence module may be configured to model more complex processing of relationships in a manner similar to a neural network, such as in a deep learning protocol. Accordingly, although in some instances, the relationships may be configured in a linear array, such as to form a direct linkage between the properties, in other instances, the relationships may be layered one on top of the other so as to form a stacked, e.g., neural, network of information.

Hence, in particular instances, the relationships may be formed in a multiplicity of stages and/or levels, where one level of information is connected to the next level of information, such as in a deep learning protocol. Additionally, the relationships between the various properties from one, or the same, level to another may be strengthened, and therefore given greater weight, or weakened, and consequently given less weight, by the machine learning protocol engaged. Accordingly, as information is processed and allocated across the properties in the different, or same, levels of the system, at each stage, a variety of different points are being given greater and greater, or lesser and lesser, weights. Hence, when given a particular input, the A/I module may more efficiently and effectively predict a given outcome more accurately based on the various different levels of weighted historical information.

For example, the AI system may be adapted so as to process information in a layered or multi-staged fashion, such as for the purpose of deep learning. Accordingly, the system may be configured to evaluate data in stages. Specifically, the AI module may be adapted such that as it examines various data, such as when performing a learning protocol, stage by stage, level by level, where each connection between data gets weighted by the system, e.g., based on historical evidence and/or characteristics of relationships. The more stages and/or levels of learning that are initiated within the system the better the weighting between junctions will be, and the deeper the learning.

Further, uploading data in stages allows for a greater convergence of data within the system. Particularly, various feature extraction paradigms may also be employed so as to better organize, weight, and analyze the most salient features of the data to be uploaded. Additionally, in order to better correlate the data, one or more users may input and/or modulate basic weighting functions, while the system itself may employ a more advanced weighting function based on active learning protocols.

For instance, a deep learning protocol may be employed in training and implementing a search function of the disclosure as discussed herein. Specifically, deep learning is a paradigm where increased levels of datasets are employed in generating an answer to a query. If there is only one stage of learning involved, when answering a query, the network architecture may be configured as a neural network.

However, if the determination implements a multi-stage learning process, when deriving an answer to a query, the architecture may be configured as a deep learning network. The more stages there are, where each stage includes a weight, the deeper the learning will be. But, with each stage added, the computing power required to make the data converge becomes greater and greater. Specifically, with each additional data set being processed, another node is generated, which increases the level of future processing power.

With respect to the present disclosure, when running a deep learning protocol, the process first implements a feature extraction protocol. In the deep learning protocol, salient features are extracted and considered in comparison with similar features stored in a database of previously extracted features. For example, each feature may represent a characteristic that may be categorized into one or more categories, classes, or labels, which labels may be used to recognize patterns. The machine can therefore be trained to recognize the reoccurrence of those patterns in other representations, and thereby draw conclusory predictions based on those recognized patterns.

Accordingly, in order to perform machine learning there needs to be a library of functions. This is useful, for instance, where anchor characterizations may be identified, such as of a problematic condition, a treatment therefore, and a claim made pursuant to the treatment. In such an instance, subsequent analysis or distribution does not need to involve analysis or distribution of the entire subsequent characterizations. Rather, only data pertaining to any differences or divergence from the anchor, such as in response to a claim being unexpectedly granted or denied. This is termed feature extraction, the preferential analysis of the anchor characterizations, or in some instances, only the deltas.

Accordingly, in various instances, methods disclosed herein are directed to using labels, e.g., pointers, to categorize and structure a database, such as for use in the artificial intelligence module to analyze data therein. In such machine learning the data may be first cleaned and prepared for feature extraction, e.g., of characteristic and/or condition and/or other significant data. Such data, once extracted may be captured with respect to an individual, a group of individuals, a population, and may be based on one feature, a plurality of features, etc. thereby building a library of features as data is coming into the system. And once the data is in the system it can be used to train the machine to build a graph assembly so s to generate potential levels of correspondences.

As indicated, the AI system may be configured for answering a query, such as from a wellness analyst and/or provider, which may or may not be a licensed physician or medical researcher. Accordingly, when performing a search function of the AI repository or database, the database may be configured as a relational database. In various instances, the architecture of that database is such that it may be structured as a table or tree, or the architecture may be configured such that data is stored therein in a graph form, such as a knowledge graph, as described above.

Additionally, when performing a search of the database, the search may be an effect based or an inference based search query. An effect based search is typically one where the outcome is known and/or expected, whereas in an inference based search, the outcome is not known. Although table based searching is useful, it is based on known relationships that are categorized by tables, which may be searched by using the known key. Such searching is generally effect based searching, where the answer is known, and the relationship with its query simply needs to be identified, e.g., via the use of the key.

Inference based searching, on the other hand, is where the relationship between two data points is unknown, but to be determined based on the building of a knowledge graph. In such an instance, the learnings of the system, with respect to other relationships and the rules of those relationships, allow for new relationships to be discovered and otherwise unknown outcomes to be determined. As such, the generation and implementation of the knowledge graph is a useful feature of the present search function in an inference based learning schema upon which the machine learning and inference engines, as herein described, are primarily built. Hence, as data flows into the database, it is formulated into one or more of these, or another, such structure, and the data, e.g., where its relationship to other data is known, may then be employed to train the search function of the system to determine data points and/or relationships between data points where the relationship was not heretofore previously known.

Specifically, once the known relationships have been determined, through a training process, the newly trained system, and the rules developed, may then be employed to infer other relationships, heretofore unknown, between the data points with a probability establishing the prediction that the inferred relationship is in fact an actual relationship. In such a manner, various conditions of a subject may be entered into the system, as one set of a collection of data points, and likewise a set of characteristics of a variety of proposed treatments may also be entered into the system as well, and this data may be employed to build a knowledge graph whereby the various relationships, known and inferred, between these data may be determined. This may be done for one or a plurality of subjects, where the relationships and the learnings therefrom may be used to determine known outcomes, such as for training the system, and once suitably trained the system may then employ these learnings in determining heretofore unknown relationships so as to infer outcomes therefrom, such as with respect to whether determined claims will be reimbursed and to what extent.

Hence, known facts and relationships may be used to train the AI engine, which once trained may determine rules by which unknown relationships may be determined and outcomes based on those relationships may be inferred and/or otherwise determined, such as by a suitably configured inference engine of the system. Particularly, an individual may be subjected to an interview process whereby one or more data points pertaining to one or more conditions affecting one or more of their conditions is described and entered into the system. Likewise, a healthcare practitioner may also be subjected to an interview process whereby one or more data points pertaining to one or more treatments for the aforementioned conditions. The system may then receive these data, and one or more features may be extracted, and one or more nodes may be formed, and may be used to generate a knowledge graph.

Accordingly, in various instances, the entered data may be reviewed by a healthcare practitioner, for verification and authentication purposes, and thus, this data is known, and therefore fact-based data. Such data, for instance, may be entered into the system, such as through a graphical user interface presented on a client computer of the system. In such a manner, one or more conditions pertinent to the individual, e.g., obtained via one or more interviews, from one or more subject's, may be entered into the system such as via a remote interface generated at an associated client computer. This condition data may be any data of significance to the individual and/or their health goals, such as health data, disease related data, healthcare prescription data, dental history, allergy data, psychological data, and the like.

As discussed herein above, the individual's medical and/or genetic data may also be uploaded into the system, and may then be correlated with one or more wellness agents determined to be relevant to one or more of the conditions. Further, in various embodiments, the individual's condition data may be from a plurality of donors, such as from a group or groups, a community or communities, from a population or populations, and the like. Further, treatment data may be any data determined by a healthcare practitioner, and determined to be of interest to treating the one or more conditions. In various instances, the system may be configured such that this data may be uploaded into the system automatically, from one or more sources.

Accordingly, the AI system server, e.g., the machine learning and inference engine implementations, may be positioned remotely from the location from where the condition is uploaded into the system, but may be accessed locally or remotely as described herein. This data serves many purposes, one such purpose being the training of the AI module, and/or its use in one or more predictive models. In such training, known relationships and outcomes can be treated as if they are unknown, and consequently the machine may be made to determine the relationships and predict the outcomes anew, which training may continue until the system has learned to predict the right outcome.

Particularly, this training, e.g., two class-model training may be used for a sub-portion of the data, e.g., 50%, the training portion, and the other data may be used to test the learnings from the training portion to predict the known outcomes, with respect to the other 50% of the data. Hence, the first portion of the data may be employed to develop a training model, and the second portion of the data may be used to test the training models to enhance the accuracy of a predictive model, which once sufficiently trained may be employed to make other inferences and thereby predict other outcomes.

For example, once trained, the inference engine may be employed to search the database in response to a user entered query and based on the known and/or inferred relationship between the various data of the system, an answer to that query may be inferred and an outcome predicted, e.g., a given request may be input into the system. Particularly, an answer may be generated by the system based on the relationships between the data. One, two, three, or more inputs may be entered into the system, in addition to a query, and an output may be determined and returned by the system.

For instance, a subject's characteristics and conditions may be correlated with their clinical data, and be uploaded into a database of potentially correlated data from other subjects. The system may perform a comparison between the characteristic and condition data of one or more subjects, such as for use in training and/or the development of predictive models. Specifically, as indicted above, the data entered into the system may be used to train the system, and once trained the system may be employed to make one or more correlations or predictions, therewith, such as in response to a query, such as with respect to whether a claim for a treatment will be reimbursed.

Accordingly, in various instances, the system may include an inference engine, such as configured as a neural network, that is adapted for receiving a plurality of inputs, performing an analysis of the data, and generate one or more correlations between the various data points. In particular instances, the system is configured for allowing the inference engine to be accessed remotely, such as via a cloud based interface accessed through a client computer. Once accessed, information pertaining to a particular subject may be uploaded onto the system, or if already uploaded may be accessed.

For instance, once uploaded, the system may feed the subject's data into a knowledge graph of the system with respect to a given population of interest. Specifically, the system may receive the subject's data, and based on an initial analysis of the data may tag and store the data in relation to one or more populations to which the data may be fit. Such groupings may be made based on a number of characteristics, including age, weight, gender, medical conditions, prescribed medicines or treatments, genetic and/or clinical profile (EMR/PHR), demographics (national origin, ethnic/religious background, sexual orientation, etc.) and the like.

This data may be uploaded into the system, and may serve as nodes for generating the knowledge graph, in relation to others in the defined population of interest, where each node may be defined by a number of properties. Once the pertinent group has been defined and the relevant properties characterized within the knowledge graph, the inference engine may then be employed so as to determine both known and inferred correlations between the various data points and/or their characteristics. Such inferences may be performed automatically, or in response to an entered query.

Particularly, in one use model, a healthcare practitioner may access the inference engine via a graphical user interface of a computer at their office. The practitioner may upload subject information, which information may be encrypted and transmitted to a central repository, e.g., server system. Once received, the encoded data may be de-encrypted, and used to build a knowledge graph, by pulling up data from other subject's that have correspondingly related characteristics so as to generate the nodes of the graph.

The physician or other healthcare provider may then enter a query by which to initiate a search of the data base. The inference engine, in response to the query, can then define the relationships between relevant nodes, and form those known relationships either return an answer, or generate, e.g., infer, further heretofore unknown relationships by which an answer may be determined and returned to the healthcare practitioner. In various instances, along with the answer, e.g., whether a claim will be covered, a predictive quality score, e.g., confidence score, as to how accurate the returned answer is expected to be may also be generated.

Based on the confidence score and/or other pertinent factors the rules that the inference engine uses to define the various relationships between particular nodes in the knowledge graph may be adjusted. For instance, these rules may be adjusted to be stricter or more lenient so as to what data points and which relationships will be considered as valid when making a given predictive model, e.g., which nodes may be considered as objects. Particularly, various of these data may be considered as subjects and predicates, and may be correlated as objects, for use in implementing one or more of the procedures referenced herein.

Hence, in a manner such as this, once a subject's conditions, and/or their genetic and/or genomic profile is known, this data may be used in relation to their clinical profile, e.g., EMR/PHR, and their claim coverage. This data may then be used so as to determine whether a particular treatment regime and/or medicine to be administered to this particular subject, will be approved by a third party obligator. This methodology may further be employed and determined in relationship to other known or unknown subjects having similar characteristics, genetic profiles, medical records, and/or other similar conditions.

The system is particularly useful when there are similar relationships between individuals having similar obligation agreements forming corresponding nodes, such as between family members, and/or between those who may or may not be suffering from the same or similar medical conditions and/or may be on the same or similar treatment regimes. Such relationships strengthen the relationships between the nodes. Likewise, the number of relationships between two or three nodes may also be used to strengthen the confidence when making a prediction between an inferred relationship between given nodes.

Consequently, once the various relationships have been defined and weighted, a predictive query, such as in the form of an "If"/"Then" statement may be made, such as where the physician enters a query into the system. Accordingly, the inference engine determines the "then" portion of the statement by employing a predictive model to generate a resultant outcome, such as based on a probability outlook. As noted above, in a manner such as this, the healthcare professional does not need to have access to identifying information for any other subject save the one they are currently representing.

Hence, the practitioner may enter their subject's conditions and/or present characteristics, and a proposed treatment plan. The inference engine may then use that data to build a knowledge graph whereby the system may then return a proposed outlook for the subject with relation to the treatment plan being covered. The system may also suggest alternative or supplemental treatments that may be useful to implement in substitution or in addition to the originally proposed treatment plan, such as where there is a better change of coverage therefore.

Particularly, the present system in this manner, will be useful in determining what treatments to administer, and other clinically relevant parameters for a subject, such as by taking into account one or more of their genetic, genomic, clinical, and other such data in relationship to one or more other data points. More particularly, the system may be configured for not only determining based on a subject's genetic makeup and other associated data, for instance, their mutational profile, what diseases they may be particularly susceptible for, but what treatments, e.g., drug prescriptions and usage, may be of benefit to the subject, e.g., given their present conditions. In various instances, certain aspects of the artificial intelligence module may be accelerated, such as by being implemented in hardware, such as by a suitably configured integrated circuit, such as by an FPGA, ASIC, Structured ASIC, and the like. For instance, in certain embodiments, the AI system may be configured to model a neural network, including a deep learning neural network, which may be formed of layers and layers or processing engines, where the more layers provided the deeper the learning configuration, and where each processing engine is trained in accordance with the methods disclosed herein to perform predictive analyses, which based on the number of layers may allow for exponential analyses to be performed.

As indicated, one or more aspects or features of the subject matter described herein may be realized in digital electronic circuitry, integrated circuitry, specially designed ASICs (application specific integrated circuits), FPGAs (field programmable gated array), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g., mouse, touch screen, etc.), and at least one output device.

These computer programs, which can also be referred to as programs, software, software applications, hardware, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" (sometimes referred to as a computer program product) refers to physically embodied apparatus and/or device, such as for example magnetic discs, optical disks, memory, and Programmable Logic Devices (PLDs), used to provide machine instructions and/or data to a programmable data processor, including a machine-readable medium that receives machine instructions as a machine-readable signal. The term "machine-readable signal" refers to any signal used to provide machine instructions and/or data to a programmable data processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

Accordingly, provided herein is a non-transitory computer readable medium that stores instructions that, when executed by one or more processors, cause the one or more processors to perform one or more of the method steps disclosed herein. For instance, the computer implemented method may include identifying a patient having one or more conditions in need of treatment, such as where the patient has an agreement with a third-party obligator that obligates the third-party obligator to pay for one or more treatments. The method may further include identifying, e.g., by the one or more computing devices, one or more conditions and/or one or more treatments to be, or having been, provided to the patient by a health care provider. Further still, the method being implemented by the one or more computing devices, may include searching for and identifying one or more provisions in the agreement that characterize one or more of the conditions and/or treatments covered by the agreement. Additionally, the method may include the one or more computing devices determining whether the treatment provided is covered by the provisions of the agreement.

Furthermore, non-transitory computer readable medium as implemented by at least one of the computing devices may include instructions for generating a claim for submittal to the third-party obligator, when it is determined that the treatment is, or at least should be, covered by one or more terms of the agreement. For example, the method may include identifying, using the one or more computing devices, one or more rules that are applicable to one or more of the conditions, treatment, and the provisions of the agreement and applying the identified rules to the treatment so as to determine whether the treatment provided is covered by the provisions of the agreement. In various instances the one or more rules may include a requirement that should be met for receiving payment on the claim, and the method may include determining that all requirements have been met, such as prior to generating a claims packet to be submitted to the third party obligator. Hence, the method to be executed may further include generating a claim packet having one or more claims for submittal to the third-party obligator. As indicated, the computer implemented instructions may further instruct one or more processing engines of the computing device to determine the accuracy of the information to be included in the claims packet, and where information may be inaccurate or missing, the method may include retrieving accurate information when it is determined that the information in the claim packet is deficient because of it being either missing or inaccurate.

To provide for interaction with a user, the subject matter described herein can be implemented on a computer having a display device, such as for example a cathode ray tube (CRT), or a liquid crystal display (LCD), or light emitting diode (LED) or (OLED) monitor for displaying information to the user and a keyboard and a pointing device, such as for example a mouse or a trackball, by which the user may provide input to the computer. In various instances, the display screen may be a capacitive sensing interactive touch-screen display. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), WiFi, and the Internet.

The computing system may include clients and servers. A client and server are generally remote from each other and typically interact through a communication network. The relationship of client and server arises by virtue of computer programs running on the respective computers and having a client-server relationship to each other.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. Other implementations may be within the scope of the following claims.

The methods illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Although a few embodiments have been described in detail above, other modifications are possible. Other embodiments may be within the scope of the following claims.

The invention claimed is:

1. A system for evaluating, processing, and submitting claims on behalf of a first patient receiving a health treatment to a third-party obligator, the system comprising:

a client computing device having a display coupled therewith and including a communications element for receiving and transmitting a first patient data packet via an associated network connection, the client computing device configured for receiving data pertaining to a treatment proposed by a healthcare provider to be administered to the first patient in order to treat one or more conditions thereof to produce the first patient data packet;

a structured database containing a plurality of searchable libraries, the plurality of libraries containing a first library including data files pertaining to an obligation agreement between the first patient and a third-party obligator, the obligation agreement including a set of terms defining a coverage for one or more treatments, and a second library including a set of rules for evaluating a level of correspondence between the obligation agreement and one or more procedures proposed to be administered in accordance with the proposed treatment, the terms of the set of terms of the obligation agreement and each rule of the set of rules being coded so as to associate each respective term and rule with a defined searchable category, the database being structured to be queried in a manner to effectuate rapid access to the first patient's obligation agreement and a subset of rules identifiable as being applicable for performing the evaluation;

a server system having a plurality of sets of processing engines at least one set of the processing engines being pretrained by an artificial intelligence (AI) module so as to from a set of pretrained processing engines, the set of pretrained processing engines being trained to determine one or more trends, each of the plurality of sets of processing engines being configured for executing one or more sets of instructions, and the at least one set of pretrained processing engines further being configured for executing one or more sets of instructions based on the one or more determined trends, the server system configured for receiving the first patient data packet and for evaluating the proposed procedures of the proposed treatment against the set of terms of the obligation agreement so as to determine the likelihood that the proposed treatment will be covered, the server system comprising:

a first set of processing engines configured for executing instructions for receiving the data packet containing the data pertaining to the proposed treatment, and for identifying the proposed procedures to be administered for the purpose of implementing the proposed treatment, each procedure having a determined cost associated therewith;

a second set of processing engines configured for executing instructions for retrieving from the structured database the obligation agreement, for identifying terms of the obligation agreement applicable to the proposed procedures, and for identifying and retrieving the subset of rules applicable for performing the evaluation, the evaluation determining a level of correspondence between the applicable terms of the obligation agreement and the proposed procedures to be administered;

a third set of processing engines comprising a first set of pretrained processing engines configured for executing instructions for performing the evaluation, comprising applying the identified subset of rules to both the identified terms of the obligation agreement and the one or more procedures proposed to be provided to determine a level of correspondence between the identified terms of the obligation agreement and the one or more procedures proposed to be administered, and if the level of correspondence falls below a determined level, identifying the one or more trends affecting application of the identified rules, and based on the one or more identified trends updating and reapplying the identified rules so as to appropriately adjust the level of correspondence;

a fourth set of processing engines comprising a second set of pretrained processing engines configured for executing instructions for determining a likelihood that the one or more procedures proposed to be administered are covered by the obligation agreement so as to produce a covered procedure plan, the likelihood determination being based partially on the one or more determined trends and the level of correspondence or the adjusted level of correspondence;

a fifth set of processing engines configured for executing instructions for determining, using the covered procedure plan, a percentage of the cost that is likely be paid on for each administered procedure to generate a total amount to be reimbursed; and a sixth set of processing engines configured for executing instructions for comparing the one or more procedures proposed to be administered with the total amount to be reimbursed and for authorizing that one or more of the proposed procedures be administered based on the likelihood that a given procedure will be covered.

2. The system in accordance with claim 1, wherein determining the likelihood that the one or more procedures proposed to be administered are covered comprises performing a mapping function, whereby the one or more conditions of the first patient and one or more of the proposed procedures of the treatment are individually mapped to one or more terms of the obligation agreement so as to define respective relationships there between, whereby each respective relationship is weighted based on previous known instances having a same or similar relationship with respect to other patients.

3. The system in accordance with claim 2, wherein the server system further comprises an inference engine configured for executing instructions for accessing one or more libraries of the structured database and determining a number of known instances whereby a second patient received a reimbursement for an administered procedure that was covered by a term of an obligation agreement for the second patient, wherein the number of known instances includes one or more of an instance of a relationship between one or more conditions of a second patient and one or more terms of an obligation agreement for the second patient, as well as an instance of a relationship between one or more proposed procedures of treatment for the second patient and the one or more terms of the obligation agreement for the second patient, where the one or more conditions, proposed procedures for treatment, or terms of the obligation agreement for the second patient are similar to those for the first patient, and whereby for each known instance, a weighting for a respective relationship used in performing the likelihood determination for the first patient is increased, where the greater the weighting the greater the likelihood is determined to be.

4. The system in accordance with claim 1, further comprising a sixth processing engine configured for executing instructions for generating and submitting an invoice to the third-party obligator, after the one or more proposed procedures have been administered to the patient, the invoice including one or more claims for reimbursement, each claim having an amount to be reimbursed, the sixth processing engine further being configured for generating a total amount to be reimbursed.

5. The system in accordance with claim 4, further comprising a seventh processing engine configured for executing instructions for determining an immediate amount to be paid to the health care provider on the one or more claims for reimbursement, the immediate amount to be paid being less than the total amount to be reimbursed.

6. The system in accordance with claim 5, wherein the client computing device includes a graphical user interface (GUI) and an input device, the GUI for presenting to the healthcare provider by an interview processing engine of the system server an interview having questions pertaining to one or more of the conditions to be treated, the procedures proposed to be administered for effectuating treatment, and the claims to be made in correspondence to the treatment.

7. The system in accordance with claim 6, wherein the interview is an interactive interview whereby answers to previously presented questions are used by the system to determine subsequent questions to be presented to the healthcare provider.

8. The system in accordance with claim 7, wherein one or more of the interview questions pertain to one or more qualifications that must be met in order for the third-party obligator to cover the claim, and the server system further includes an error generating processing engine that is configured for flagging each instance where a conflict results in a qualification not being met, wherein for each flag the interview processing engine generates a new question pertaining to resolving the conflict.

9. The system in accordance with claim 8, wherein the server system further includes an authorization engine configured for executing instructions for authorizing the treatment when there is a likelihood that the one or more proposed procedures to be taken will be covered, and further wherein the server system includes a communications element configured for transmitting the authorization to the healthcare provider via the associated network connection of the client computing device.

10. The system in accordance with claim 9, wherein the server system further comprises an inference engine configured for executing instructions for determining if there is a conflict between a treatment proposed to be administered and an obligation to cover the treatment, and when a conflict is present, the inference engine determines one or more possible solutions to the conflict, transmits the one or more possible solutions to the healthcare provider via the associated network connection of the client computing device, and initiates a hold preventing the invoice from being submitted to the third party obligator until the conflict is resolved.

11. The system in accordance with claim 10, wherein the first patient data packet includes a description of the characteristics of the first patient, the one or more conditions of the first patient, the proposed procedures of the treatment to be administered to the first patient, and one or more of the terms of the obligation agreement for the first patient, and further wherein the structured database includes a rules library containing the sets of rules, such that the likelihood determination is based on applying at least one of the sets of rules to one or more of the one or more conditions of the patient, the proposed treatment to be administered to the patient, and the terms of the obligation agreement for the first patient.

12. The system in accordance with claim 11, wherein the plurality of rules are determined by a law, a statute, a regulation, a government ordinance, a policy, a practice, a procedure, or a principle.

13. The system in accordance with claim 12, wherein when at least one of the sets of rules support a relationship between the one or more conditions of the first patient and the proposed treatment to be administered to the first patient, then the instance of that relationship is given more weight, and when at least one of the sets of rules does not support the relationship between the one or more conditions of the patient and the proposed treatment to be administered to the first patient, then the instance of the relationship is given less weight.

14. The system in accordance with claim 13, wherein when at least one of the sets of rules support a relationship between the proposed treatment to be administered to the patient and the one or more terms of the obligation agreement, then the instance of that relationship is given more weight, and when at least one of the sets of rules does not support the relationship between the proposed treatment to be administered to the patient and the one or more terms of the obligation agreement, then the instance of that relationship is given less weight.

15. The system in accordance with claim 14, wherein when a conflict arises between a rule and one or more of proposed treatment to be administered and a term of the obligation agreement, then the instance between the proposed treatment to be administered to the first patient and the one or more terms of the obligation agreement is given less weight.

16. A system for evaluating and processing claims on behalf of a patient receiving a health treatment, the system comprising:
a client computing device having a display coupled therewith, the display for displaying a graphical user interface to a first individual using the client computing device, the graphical user interface for generating an interactive dashboard for presentation via the display, the interactive dashboard configured for presenting a claims interview to the first individual and for receiving responses thereto from the first individual, the claims interview pertaining to a treatment proposed to be administered to a patient in order to treat one or more conditions thereof so as to produce a patient data packet, the client computing device including a communications element for transmitting the patient data packet via an associated network connection;
a structured database, coupled to the client computing device via a network connection, the structured database containing a plurality of searchable libraries, the plurality of libraries containing a first library including data files pertaining to an obligation agreement between the patient and a third-party obligator, the obligation agreement including a set of terms defining a coverage for one or more treatments, and a second library including a set of rules for evaluating a level of correspondence between the obligation agreement and one or more procedures proposed to be administered in accordance with the proposed treatment, the terms of the set of terms of the obligation agreement and the rules of the set of rules being coded so as to associate each respective term and rule with a defined searchable category, the database being structured to be queried in a manner to effectuate rapid access to the patient's obligation agreement and a subset of rules identifiable as being applicable for performing the evaluation;
a server system coupled to both the structured database and the client computing device via the network connection, the server system having a set of processing engines for executing one or more sets of instructions, the server system configured for generating a project builder, the project builder for providing the graphical user interface to the client computing device via the network connection for local display thereby, the server system being configured for executing one or more sets of instructions for:
generating, by a first set of processing engines implementing a first set of instructions, the client interview for display at the graphical user interface via the interactive dashboard, the client interview including one or more interrogatories that are configured for eliciting one or more responses from the first individual, the one or more responses being used to produce the patient data packet;
receiving, by the server system, the produced patient data packet from the interactive dashboard via the network connection and for employing the patient data packet in the creation of an individualistic characteristic profile for the patient, the individualistic characteristic profile including a characterization of one or more conditions of the patient, one or more treatments proposed to be administered to the patient to alleviate the one or more conditions, and one or more terms of the obligation agreement determined to be pertinent to one or more of the conditions of the patient and the one or more treatments proposed to be administered, the one or more proposed treatments having a cost being associated therewith;
performing, by a first set of pretrained processing engines implementing a second set of instructions, using the individualistic characteristic profile for the patient, an evaluation, the first set of pretrained processing engines being pretrained by an artificial intelligence (AI) module to identify one or more trends for efficiently performing the evaluation, the evaluation comprising:
applying the identified subset of rules to both the identified terms of the obligation agreement and the one or more procedures proposed to be provided to determine a level of correspondence between the identified terms of the obligation agreement and the one or more procedures proposed to be administered, and if the level of correspondence falls below a determined level, identifying, by the first set of pretrained processing engines, one or more trends affecting the application of the identified rules, and based on the one or more identified trends updating and reapplying the identified rules so as to appropriately adjust the level of correspondence;
determining, by a third set of processing engines, based on the evaluation, a likelihood that the one or more proposed procedures to be administered are covered by the obligation agreement so as to produce a covered procedure plan, the likelihood determination being based partially on the level of correspondence or the adjusted level of correspondence;
determining, by a fourth set of processing engines, using the covered procedure plan, a percentage of the cost that is likely be paid for each administered procedure of the proposed procedures so as to generate a total amount to be reimbursed; and comparing, by a fifth set of processing engines, the one or more proposed procedures to be administered with the total amount to be reimbursed, and for authorizing one or more of the proposed procedures to be administered based on the likelihood that one or more proposed procedures will be covered.

17. The system in accordance with claim 16, wherein determining the likelihood that the one or more proposed procedures to be administered are covered comprises: performing a mapping function, whereby the one or more conditions of the patient and one or more of the proposed procedures to be administered are individually mapped to one or more terms of the obligation agreement so as to define respective relationships there between, whereby each respective relationship is weighted based on previous known instances having the same or similar relationship with respect to other patients.

18. The system in accordance with claim 17, wherein the server system further comprises an inference engine configured for executing instructions for accessing one or more libraries of the structured database and determining a number of known instances whereby other patients received a reimbursement for an administered procedure that was covered by a term of an obligation agreement for the other patients, wherein the number of known instances includes one or more of an instance of a relationship between one or more conditions of the other patient and one or more terms of an obligation agreement of that other patient, as well as an instance of a relationship between one or more proposed procedures administered to the other patient and the one or more terms of the obligation agreement for the other patient, where the one or more conditions, proposed procedures for treatment, or terms of the obligation agreement for the other patient are similar to those for the first patient, and whereby for each known instance, a weighting for a respective relationship used in performing the likelihood determination for the first patient is increased, where the greater the weighting the greater the likelihood is determined to be.

19. The system in accordance with claim 18, wherein the server system is further configured for generating and submitting an invoice to the third-party obligator, after one or more procedures have been administered to the patient, the invoice including one or more claims for reimbursement, each claim having an amount to be reimbursed, the server system further being configured for generating a total amount to be reimbursed.

20. The system in accordance with claim 18, wherein the interview is an interactive claims interview whereby answers to previously presented questions are used by the system to determine subsequent questions to be presented to the healthcare provider.

* * * * *